US012343117B2

(12) United States Patent
Misener et al.

(10) Patent No.: US 12,343,117 B2
(45) Date of Patent: Jul. 1, 2025

(54) FIBER OPTIC MEDICAL SYSTEMS AND METHODS FOR IDENTIFYING BLOOD VESSELS

(71) Applicant: Bard Access Systems, Inc., Salt Lake City, UT (US)

(72) Inventors: Anthony K. Misener, Bountiful, UT (US); Shayne Messerly, Kaysville, UT (US); Steffan Sowards, Salt Lake City, UT (US); William Robert McLaughlin, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 198 days.

(21) Appl. No.: 17/852,138

(22) Filed: Jun. 28, 2022

(65) Prior Publication Data

US 2023/0414112 A1    Dec. 28, 2023

(51) Int. Cl.
*A61B 5/02* (2006.01)
*A61B 5/00* (2006.01)
(Continued)

(52) U.S. Cl.
CPC ........ *A61B 5/02007* (2013.01); *A61B 5/6852* (2013.01); *A61B 8/488* (2013.01); *A61B 34/20* (2016.02)

(58) Field of Classification Search
CPC ... A61B 5/02007; A61B 5/6852; A61B 8/488; A61B 34/20; A61B 2562/0233;
(Continued)

(56) References Cited

U.S. PATENT DOCUMENTS

| 4,813,429 A | 3/1989 | Eshel et al. |
|---|---|---|
| 5,099,845 A | 3/1992 | Besz et al. |

(Continued)

FOREIGN PATENT DOCUMENTS

| CN | 101132730 A | 2/2008 |
|---|---|---|
| CN | 111265309 A | 6/2020 |

(Continued)

OTHER PUBLICATIONS

U.S. Appl. No. 15/947,267, filed Apr. 6, 2018 Notice of Allowance dated Jul. 16, 2024.
(Continued)

*Primary Examiner* — Sanjay Cattungal
(74) *Attorney, Agent, or Firm* — Rutan & Tucker LLP

(57) ABSTRACT

Disclosed herein are medical systems, devices, and methods for identifying a blood vessel as a vein or as an artery. The system includes an optical fiber configured for insertion into a blood vessel coupled with a console having a light source, an optical receiver, processors, and logic stored in memory. The optical fiber includes sensors disposed along its length configured to determine a state or condition of the optical fiber, where the state or condition includes a strain, movement, pressure, or temperature. The logic analyzes reflected optical signals emanating from the sensors to determine that the optical fiber is inserted within an artery or within a vein. Logic may also determine a red-blue shift of a projected light to determine a blood flow direction with respect to the optical fiber.

20 Claims, 11 Drawing Sheets

(51) Int. Cl.
*A61B 8/00* (2006.01)
*A61B 34/20* (2016.01)

(58) Field of Classification Search
CPC .... A61B 2562/0247; A61B 2562/0266; A61B 5/02154; A61B 5/0084; A61B 5/0215; A61B 1/00165; A61B 1/0684; A61B 5/01
See application file for complete search history.

(56) References Cited

U.S. PATENT DOCUMENTS

| | | | |
|---|---|---|---|
| 5,163,935 A | 11/1992 | Black et al. | |
| 5,207,672 A | 5/1993 | Roth et al. | |
| 5,211,165 A | 5/1993 | Dumoulin et al. | |
| 5,275,151 A | 1/1994 | Shockey et al. | |
| 5,280,786 A | 1/1994 | Wlodarczyk et al. | |
| 5,423,321 A | 6/1995 | Fontenot | |
| 5,454,807 A | 10/1995 | Lennox et al. | |
| 5,460,182 A | 10/1995 | Goodman et al. | |
| 5,517,997 A | 5/1996 | Fontenot | |
| 5,622,170 A | 4/1997 | Schulz | |
| 5,740,808 A | 4/1998 | Panescu et al. | |
| 5,841,131 A | 11/1998 | Schroeder et al. | |
| 5,872,879 A | 2/1999 | Hamm | |
| 5,873,842 A | 2/1999 | Brennen et al. | |
| 5,879,306 A | 3/1999 | Fontenot et al. | |
| 5,906,579 A | 5/1999 | Vander Salm et al. | |
| 6,069,698 A | 5/2000 | Ozawa et al. | |
| 6,081,741 A | 6/2000 | Hollis | |
| 6,178,346 B1 | 1/2001 | Amundson et al. | |
| 6,208,887 B1 | 3/2001 | Clarke | |
| 6,319,227 B1 | 11/2001 | Mansouri-Ruiz | |
| 6,343,227 B1 | 1/2002 | Crowley | |
| 6,398,721 B1 | 6/2002 | Nakamura et al. | |
| 6,485,482 B1 | 11/2002 | Belef | |
| 6,564,089 B2 | 5/2003 | Izatt et al. | |
| 6,593,884 B1 | 7/2003 | Gilboa et al. | |
| 6,597,941 B2 | 7/2003 | Fontenot et al. | |
| 6,650,923 B1 | 11/2003 | Lesh et al. | |
| 6,673,214 B1 * | 1/2004 | Marchitto | B01J 19/129 |
| | | | 204/157.15 |
| 6,685,666 B1 | 2/2004 | Fontenot | |
| 6,687,010 B1 | 2/2004 | Horii et al. | |
| 6,690,966 B1 | 2/2004 | Rava et al. | |
| 6,701,181 B2 | 3/2004 | Tang et al. | |
| 6,711,426 B2 | 3/2004 | Benaron et al. | |
| 6,816,743 B2 | 11/2004 | Moreno et al. | |
| 6,892,090 B2 | 5/2005 | Verard et al. | |
| 6,895,267 B2 | 5/2005 | Panescu et al. | |
| 7,132,645 B2 | 11/2006 | Kom | |
| 7,273,056 B2 | 9/2007 | Wilson et al. | |
| 7,344,533 B2 | 3/2008 | Pearson et al. | |
| 7,366,562 B2 | 4/2008 | Dukesherer et al. | |
| 7,366,563 B2 | 4/2008 | Kleen et al. | |
| 7,396,354 B2 | 7/2008 | Rychnovsky et al. | |
| 7,406,346 B2 | 7/2008 | Kleen et al. | |
| 7,515,265 B2 | 4/2009 | Alfano et al. | |
| 7,532,920 B1 | 5/2009 | Ainsworth et al. | |
| 7,587,236 B2 | 9/2009 | Demos et al. | |
| 7,603,166 B2 | 10/2009 | Casscells, III et al. | |
| 7,729,735 B1 | 6/2010 | Burchman | |
| 7,757,695 B2 | 7/2010 | Wilson et al. | |
| 7,758,499 B2 | 7/2010 | Adler | |
| 7,840,253 B2 | 11/2010 | Tremblay et al. | |
| 7,992,573 B2 | 8/2011 | Wilson et al. | |
| 8,032,200 B2 | 10/2011 | Tearney et al. | |
| 8,054,469 B2 | 11/2011 | Nakabayashi et al. | |
| 8,060,187 B2 | 11/2011 | Marshik-Geurts et al. | |
| 8,073,517 B1 | 12/2011 | Burchman | |
| 8,078,261 B2 | 12/2011 | Imam | |
| 8,187,189 B2 | 5/2012 | Jung et al. | |
| 8,267,932 B2 | 9/2012 | Baxter et al. | |
| 8,369,932 B2 | 2/2013 | Cinbis et al. | |
| 8,388,541 B2 | 3/2013 | Messerly et al. | |
| 8,571,640 B2 | 10/2013 | Holman | |
| 8,597,315 B2 | 12/2013 | Snow et al. | |
| 8,700,358 B1 | 4/2014 | Parker, Jr. | |
| 8,781,555 B2 | 7/2014 | Burnside et al. | |
| 8,798,721 B2 | 8/2014 | Dib | |
| 8,968,331 B1 | 3/2015 | Sochor | |
| 8,979,871 B2 | 3/2015 | Tyc et al. | |
| 9,060,687 B2 | 6/2015 | Yamanaka et al. | |
| 9,114,226 B1 | 8/2015 | Lash et al. | |
| 9,206,309 B2 | 12/2015 | Appleby et al. | |
| 9,360,630 B2 | 6/2016 | Jenner et al. | |
| 9,504,392 B2 | 11/2016 | Caron et al. | |
| 9,560,954 B2 | 2/2017 | Jacobs et al. | |
| 9,622,706 B2 | 4/2017 | Dick et al. | |
| 9,678,275 B1 | 6/2017 | Griffin | |
| 10,231,753 B2 | 3/2019 | Burnside et al. | |
| 10,258,240 B1 | 4/2019 | Eberle et al. | |
| 10,327,830 B2 | 6/2019 | Grant et al. | |
| 10,349,890 B2 | 7/2019 | Misener et al. | |
| 10,492,876 B2 | 12/2019 | Anastassiou et al. | |
| 10,568,586 B2 | 2/2020 | Begin et al. | |
| 10,631,718 B2 | 4/2020 | Petroff et al. | |
| 10,992,078 B2 | 4/2021 | Thompson et al. | |
| 11,123,047 B2 | 9/2021 | Jaffer et al. | |
| 11,525,670 B2 | 12/2022 | Messerly et al. | |
| 2001/0014793 A1 | 8/2001 | Brugger et al. | |
| 2002/0198457 A1 | 12/2002 | Tearney et al. | |
| 2003/0092995 A1 | 5/2003 | Thompson | |
| 2004/0129555 A1 * | 7/2004 | Marchitto | B01J 3/08 |
| | | | 204/157.15 |
| 2004/0161362 A1 * | 8/2004 | Bogert | A61L 2/02 |
| | | | 422/1 |
| 2004/0242995 A1 | 12/2004 | Maschke | |
| 2005/0033264 A1 | 2/2005 | Redinger | |
| 2005/0163424 A1 | 7/2005 | Chen | |
| 2005/0261598 A1 | 11/2005 | Banet et al. | |
| 2005/0278010 A1 | 12/2005 | Richardson | |
| 2006/0013523 A1 | 1/2006 | Childers et al. | |
| 2006/0015136 A1 | 1/2006 | Besselink | |
| 2006/0036164 A1 | 2/2006 | Wilson et al. | |
| 2006/0189959 A1 | 8/2006 | Schneiter | |
| 2006/0200049 A1 | 9/2006 | Leo et al. | |
| 2006/0241395 A1 | 10/2006 | Kruger et al. | |
| 2006/0241492 A1 | 10/2006 | Boese et al. | |
| 2007/0156019 A1 | 7/2007 | Larkin et al. | |
| 2007/0201793 A1 | 8/2007 | Askins et al. | |
| 2007/0287886 A1 | 12/2007 | Saadat | |
| 2007/0287934 A1 * | 12/2007 | Babaev | A61B 17/320068 |
| | | | 601/2 |
| 2007/0299425 A1 | 12/2007 | Waner et al. | |
| 2008/0039715 A1 | 2/2008 | Wilson et al. | |
| 2008/0077225 A1 | 3/2008 | Carlin et al. | |
| 2008/0082004 A1 | 4/2008 | Banet et al. | |
| 2008/0172119 A1 | 7/2008 | Yamasaki et al. | |
| 2008/0183128 A1 | 7/2008 | Morriss et al. | |
| 2008/0212082 A1 | 9/2008 | Froggatt et al. | |
| 2008/0285909 A1 | 11/2008 | Younge et al. | |
| 2008/0319290 A1 | 12/2008 | Mao et al. | |
| 2009/0054908 A1 | 2/2009 | Zand et al. | |
| 2009/0062634 A1 | 3/2009 | Say et al. | |
| 2009/0118612 A1 | 5/2009 | Grunwald et al. | |
| 2009/0137952 A1 | 5/2009 | Ramamurthy et al. | |
| 2009/0234328 A1 | 9/2009 | Cox et al. | |
| 2009/0304582 A1 | 12/2009 | Rousso et al. | |
| 2009/0314925 A1 | 12/2009 | Van Vorhis et al. | |
| 2010/0016729 A1 | 1/2010 | Futrell | |
| 2010/0030063 A1 | 2/2010 | Lee et al. | |
| 2010/0030132 A1 * | 2/2010 | Niezgoda | A61M 1/73 |
| | | | 604/289 |
| 2010/0063534 A1 | 3/2010 | Kugler et al. | |
| 2010/0114115 A1 | 5/2010 | Schlesinger et al. | |
| 2010/0286531 A1 | 11/2010 | Ryan et al. | |
| 2010/0312095 A1 | 12/2010 | Jenkins et al. | |
| 2011/0060229 A1 | 3/2011 | Hulvershorn et al. | |
| 2011/0090486 A1 | 4/2011 | Udd | |
| 2011/0144481 A1 | 6/2011 | Feer et al. | |
| 2011/0166442 A1 | 7/2011 | Sarvazyan | |
| 2011/0172591 A1 * | 7/2011 | Babaev | A61M 35/30 |
| | | | 604/24 |
| 2011/0172680 A1 | 7/2011 | Younge et al. | |

(56) References Cited

U.S. PATENT DOCUMENTS

| | | |
|---|---|---|
| 2011/0237958 A1 | 9/2011 | Onimura |
| 2011/0242532 A1 | 10/2011 | McKenna |
| 2011/0245662 A1 | 10/2011 | Eggers et al. |
| 2011/0288405 A1* | 11/2011 | Razavi .................. G01L 1/246 600/424 |
| 2011/0295108 A1 | 12/2011 | Cox et al. |
| 2011/0313280 A1 | 12/2011 | Govari et al. |
| 2012/0046562 A1 | 2/2012 | Powers et al. |
| 2012/0065481 A1 | 3/2012 | Hunter et al. |
| 2012/0101413 A1 | 4/2012 | Beetel et al. |
| 2012/0136242 A1 | 5/2012 | Qi et al. |
| 2012/0143029 A1 | 6/2012 | Silverstein et al. |
| 2012/0184827 A1 | 7/2012 | Shwartz et al. |
| 2012/0184955 A1 | 7/2012 | Pivotto et al. |
| 2012/0283747 A1 | 11/2012 | Popovic |
| 2012/0289783 A1 | 11/2012 | Duindam et al. |
| 2012/0321243 A1 | 12/2012 | Younge et al. |
| 2013/0028554 A1 | 1/2013 | Wong et al. |
| 2013/0072943 A1 | 3/2013 | Parmar |
| 2013/0096482 A1 | 4/2013 | Bertrand et al. |
| 2013/0104884 A1 | 5/2013 | Vazales et al. |
| 2013/0188855 A1 | 7/2013 | Desjardins et al. |
| 2013/0204124 A1 | 8/2013 | Duindam et al. |
| 2013/0211246 A1 | 8/2013 | Parasher |
| 2013/0296693 A1 | 11/2013 | Wenzel et al. |
| 2013/0310668 A1 | 11/2013 | Young |
| 2013/0317372 A1 | 11/2013 | Eberle et al. |
| 2013/0324840 A1 | 12/2013 | Zhongping et al. |
| 2014/0121468 A1 | 5/2014 | Eichenholz |
| 2014/0221829 A1 | 8/2014 | Maitland et al. |
| 2014/0275997 A1 | 9/2014 | Chopra et al. |
| 2015/0029511 A1 | 1/2015 | Hooft et al. |
| 2015/0031987 A1 | 1/2015 | Pameijer et al. |
| 2015/0080688 A1 | 3/2015 | Cinbis et al. |
| 2015/0099979 A1 | 4/2015 | Caves et al. |
| 2015/0119700 A1 | 4/2015 | Liang et al. |
| 2015/0124264 A1 | 5/2015 | Ramachandran et al. |
| 2015/0141854 A1 | 5/2015 | Eberle et al. |
| 2015/0164571 A1 | 6/2015 | Saadat |
| 2015/0190221 A1 | 7/2015 | Schaefer et al. |
| 2015/0209113 A1 | 7/2015 | Burkholz et al. |
| 2015/0209117 A1 | 7/2015 | Flexman et al. |
| 2015/0254526 A1 | 9/2015 | Denissen |
| 2015/0320977 A1 | 11/2015 | Vitullo et al. |
| 2016/0018602 A1 | 1/2016 | Govari et al. |
| 2016/0067449 A1 | 3/2016 | Misener et al. |
| 2016/0102969 A1 | 4/2016 | Verstege et al. |
| 2016/0166326 A1 | 6/2016 | Bakker et al. |
| 2016/0166341 A1 | 6/2016 | Iordachita et al. |
| 2016/0184020 A1 | 6/2016 | Kowalewski et al. |
| 2016/0213432 A1 | 7/2016 | Flexman et al. |
| 2016/0331461 A1 | 11/2016 | Cheatham, III et al. |
| 2016/0349044 A1 | 12/2016 | Marell et al. |
| 2016/0354038 A1 | 12/2016 | Demirtas et al. |
| 2017/0020394 A1 | 1/2017 | Harrington |
| 2017/0079681 A1 | 3/2017 | Burnside et al. |
| 2017/0082806 A1 | 3/2017 | Van Der Mark et al. |
| 2017/0151027 A1 | 6/2017 | Walker et al. |
| 2017/0173349 A1 | 6/2017 | Pfleiderer et al. |
| 2017/0196479 A1 | 7/2017 | Liu et al. |
| 2017/0201036 A1 | 7/2017 | Cohen et al. |
| 2017/0215973 A1 | 8/2017 | Flexman et al. |
| 2017/0231699 A1 | 8/2017 | Flexman et al. |
| 2017/0273542 A1 | 9/2017 | Au |
| 2017/0273565 A1 | 9/2017 | Ma et al. |
| 2017/0273628 A1 | 9/2017 | Ofek et al. |
| 2017/0290563 A1 | 10/2017 | Cole et al. |
| 2017/0311901 A1 | 11/2017 | Zhao et al. |
| 2017/0319279 A1 | 11/2017 | Fish et al. |
| 2018/0008443 A1 | 1/2018 | Cole et al. |
| 2018/0031493 A1 | 2/2018 | Tojo et al. |
| 2018/0095231 A1 | 4/2018 | Lowell et al. |
| 2018/0113038 A1 | 4/2018 | Janabi-Sharifi et al. |
| 2018/0116551 A1 | 5/2018 | Newman et al. |
| 2018/0140170 A1 | 5/2018 | Van Putten et al. |
| 2018/0235709 A1 | 8/2018 | Donhowe et al. |
| 2018/0239124 A1 | 8/2018 | Naruse et al. |
| 2018/0240237 A1 | 8/2018 | Donhowe et al. |
| 2018/0250088 A1 | 9/2018 | Brennan et al. |
| 2018/0264227 A1 | 9/2018 | Flexman et al. |
| 2018/0279909 A1 | 10/2018 | Noonan et al. |
| 2018/0289390 A1 | 10/2018 | Amorizzo et al. |
| 2018/0289927 A1 | 10/2018 | Messerly |
| 2018/0339134 A1 | 11/2018 | Leo |
| 2018/0360545 A1 | 12/2018 | Cole et al. |
| 2019/0059743 A1 | 2/2019 | Ramachandran et al. |
| 2019/0110844 A1 | 4/2019 | Misener et al. |
| 2019/0231272 A1 | 8/2019 | Yamaji |
| 2019/0237902 A1 | 8/2019 | Thompson et al. |
| 2019/0247132 A1 | 8/2019 | Harks et al. |
| 2019/0307331 A1 | 10/2019 | Saadat et al. |
| 2019/0321110 A1 | 10/2019 | Grunwald et al. |
| 2019/0343424 A1 | 11/2019 | Blumenkranz et al. |
| 2019/0343702 A1* | 11/2019 | Smith .................. A61M 21/02 |
| 2019/0357875 A1 | 11/2019 | Qi et al. |
| 2019/0365199 A1 | 12/2019 | Zhao et al. |
| 2019/0374130 A1 | 12/2019 | Bydlon et al. |
| 2020/0000526 A1 | 1/2020 | Zhao |
| 2020/0030575 A1 | 1/2020 | Bogusky et al. |
| 2020/0046434 A1 | 2/2020 | Graetzel et al. |
| 2020/0054399 A1 | 2/2020 | Duindam et al. |
| 2020/0121482 A1 | 4/2020 | Spector et al. |
| 2020/0188036 A1 | 6/2020 | Ding et al. |
| 2020/0297442 A1 | 9/2020 | Adebar et al. |
| 2020/0305983 A1 | 10/2020 | Yampolsky et al. |
| 2020/0315770 A1 | 10/2020 | Dupont et al. |
| 2020/0394789 A1* | 12/2020 | Freund .................. G06T 7/0012 |
| 2021/0015470 A1 | 1/2021 | Prisco et al. |
| 2021/0023341 A1 | 1/2021 | Decheek et al. |
| 2021/0045814 A1 | 2/2021 | Thompson et al. |
| 2021/0068911 A1 | 3/2021 | Walker et al. |
| 2021/0298680 A1 | 3/2021 | Sowards et al. |
| 2021/0100627 A1 | 4/2021 | Soper et al. |
| 2021/0244311 A1 | 8/2021 | Zhao et al. |
| 2021/0268229 A1 | 9/2021 | Sowards et al. |
| 2021/0271035 A1 | 9/2021 | Sowards et al. |
| 2021/0275257 A1 | 9/2021 | Prior et al. |
| 2021/0330399 A1 | 10/2021 | Netravali et al. |
| 2021/0401456 A1 | 12/2021 | Cox et al. |
| 2021/0401509 A1 | 12/2021 | Misener et al. |
| 2021/0402144 A1 | 12/2021 | Messerly |
| 2022/0011192 A1 | 1/2022 | Misener et al. |
| 2022/0034733 A1 | 2/2022 | Misener et al. |
| 2022/0079683 A1 | 3/2022 | Bydlon et al. |
| 2022/0096796 A1 | 3/2022 | McLaughlin et al. |
| 2022/0110508 A1 | 4/2022 | Van Roosbroeck et al. |
| 2022/0110695 A1 | 4/2022 | Sowards et al. |
| 2022/0151568 A1* | 5/2022 | Yao .................. G16H 50/20 |
| 2022/0152349 A1 | 5/2022 | Sowards et al. |
| 2022/0160209 A1 | 5/2022 | Sowards et al. |
| 2022/0172354 A1 | 6/2022 | Misener et al. |
| 2022/0211442 A1 | 7/2022 | McLaughlin et al. |
| 2022/0233246 A1 | 7/2022 | Misener et al. |
| 2022/0369934 A1 | 11/2022 | Sowards et al. |
| 2023/0081198 A1 | 3/2023 | Sowards et al. |
| 2023/0097431 A1 | 3/2023 | Sowards et al. |
| 2023/0101030 A1 | 3/2023 | Misener et al. |
| 2023/0108604 A1 | 4/2023 | Messerly et al. |
| 2023/0126813 A1 | 4/2023 | Sowards et al. |
| 2023/0243715 A1 | 8/2023 | Misener et al. |
| 2023/0248444 A1 | 8/2023 | Misener et al. |
| 2023/0251150 A1 | 8/2023 | Misener et al. |
| 2023/0337985 A1 | 10/2023 | Sowards et al. |
| 2023/0346479 A1 | 11/2023 | Muller et al. |
| 2024/0000515 A1 | 1/2024 | Misener et al. |
| 2024/0050708 A1 | 2/2024 | Misener |
| 2024/0099659 A1 | 3/2024 | Sowards et al. |
| 2024/0108856 A1 | 4/2024 | Messerly |
| 2024/0216077 A1 | 7/2024 | Thompson et al. |
| 2024/0335237 A1 | 10/2024 | Sowards et al. |
| 2024/0353275 A1 | 10/2024 | Misener et al. |
| 2024/0383133 A1 | 11/2024 | Bydlon et al. |

(56) References Cited

U.S. PATENT DOCUMENTS

| | | |
|---|---|---|
| 2024/0390644 A1 | 11/2024 | McLaughlin et al. |
| 2025/0020453 A1 | 1/2025 | Thompson et al. |
| 2025/0060266 A1 | 2/2025 | Messerly |

FOREIGN PATENT DOCUMENTS

| | | |
|---|---|---|
| CN | 113080937 A | 7/2021 |
| DE | 102016109601 A1 | 11/2017 |
| EP | 2240111 A2 | 10/2010 |
| EP | 2907445 A1 | 8/2015 |
| EP | 3545849 A1 | 10/2019 |
| EP | 3705020 A1 | 9/2020 |
| JP | 7366562 B2 | 10/2023 |
| KR | 20190098512 A | 8/2019 |
| WO | 99/64099 A1 | 12/1999 |
| WO | 2006113394 A2 | 10/2006 |
| WO | 2006122001 A2 | 11/2006 |
| WO | 2007002323 A2 | 1/2007 |
| WO | 2009/155325 A2 | 12/2009 |
| WO | 2011121516 A2 | 10/2011 |
| WO | 2011141830 A1 | 11/2011 |
| WO | 2011150376 A1 | 12/2011 |
| WO | 2012064769 A2 | 5/2012 |
| WO | 2015044930 A1 | 4/2015 |
| WO | 2015074045 A2 | 5/2015 |
| WO | 2016038492 A1 | 3/2016 |
| WO | 2016/061431 A1 | 4/2016 |
| WO | 2016051302 A1 | 4/2016 |
| WO | 2016149819 A1 | 9/2016 |
| WO | 2018/096491 A1 | 5/2018 |
| WO | 2019037071 A1 | 2/2019 |
| WO | 2019/046769 A1 | 3/2019 |
| WO | 2019070423 A1 | 4/2019 |
| WO | 2019230713 A1 | 12/2019 |
| WO | 2020/182997 A1 | 9/2020 |
| WO | 2021030092 A1 | 2/2021 |
| WO | 2021108688 A1 | 6/2021 |
| WO | 2021108697 A1 | 6/2021 |
| WO | 2021/138096 A1 | 7/2021 |
| WO | 2021216089 A1 | 10/2021 |
| WO | 2022/031613 A1 | 2/2022 |
| WO | 2022/081723 A1 | 4/2022 |
| WO | 2022150411 A1 | 7/2022 |
| WO | 2022/164902 A1 | 8/2022 |
| WO | 2022/245987 A1 | 11/2022 |
| WO | 2023043954 A1 | 3/2023 |
| WO | 2023049443 A1 | 3/2023 |
| WO | 2023055810 A1 | 4/2023 |
| WO | 2023076143 A1 | 5/2023 |
| WO | 2023211752 A1 | 11/2023 |
| WO | 2024006384 A1 | 1/2024 |
| WO | 2024006441 A1 | 1/2024 |
| WO | 2024064334 A1 | 3/2024 |

OTHER PUBLICATIONS

U.S. Appl. No. 17/484,960, filed Sep. 24, 2021 Notice of Allowance dated Apr. 12, 2024.
U.S. Appl. No. 17/569,350, filed Jan. 5, 2022 Advisory Action dated Jul. 12, 2024.
U.S. Appl. No. 17/569,350, filed Jan. 5, 2022 Final Office Action dated Apr. 23, 2024.
U.S. Appl. No. 17/747,903, filed May 18, 2022 Restriction Requirement dated May 28, 2024.
U.S. Appl. No. 17/955,019, filed Sep. 28, 2022 Restriction Requirement dated Jun. 6, 2024.
U.S. Appl. No. 18/079,653, filed Dec. 12, 2022 Non-Final Office Action dated Feb. 6, 2024.
U.S. Appl. No. 18/079,653, filed Dec. 12, 2022 Notice of Allowance dated Jun. 4, 2024.
U.S. Appl. No. 18/132,231, filed Apr. 7, 2023 Non-Final Office Action dated Jul. 12, 2024.
U.S. Appl. No. 18/132,623, filed Apr. 10, 2023, Non-Final Office Action dated May 3, 2024.
U.S. Appl. No. 18/135,337, filed Apr. 17, 2023 Notice of Allowance dated Mar. 8, 2024.
U.S. Appl. No. 17/971,873, filed Oct. 24, 2022 Non-Final Office Action dated Jun. 6, 2024.
Fiber Optic RealShape (FORS) technology—research. Philips. (Oct. 18, 2018). Retrieved Feb. 28, 2023, from https:// www.philips.com/a-w/research/research-programs/fors.html (Year: 2018).
U.S. Appl. No. 16/984,104, filed Aug. 3, 2020 Restriction Requirement dated Mar. 13, 2023.
U.S. Appl. No. 17/105,310, filed Nov. 25, 2020 Non-Final Office Action dated Feb. 22, 2023.
U.S. Appl. No. 17/357,186, filed Jun. 24, 2021 Restriction Requirement dated Mar. 7, 2023.
U.S. Appl. No. 17/392,002, filed Aug. 2, 2021, Corrected Notice of Allowability dated Feb. 23, 2023.
U.S. Appl. No. 17/500,678, filed Oct. 13, 2021 Non-Final Office Action dated Mar. 15, 2023.
Jackle Sonja et al. "Three-dimensional guidance including shape sensing of a stentgraft system for endovascular aneurysm repair." International Journal of Computer Assisted Radiology and Surgery, Springer DE. vol. 15, No. 6, May 7, 2020.
PCT/US2022/029894 filed May 18, 2022, International Search Report and Written Opinion dated Sep. 1, 2022.
PCT/US2022/043706 filed Sep. 16, 2022 International Search Report and Written Opinion dated Nov. 24, 2022.
PCT/US2022/044696 filed Sep. 26, 2022 International Search Report and Written Opinion dated Jan. 23, 2023.
PCT/US2022/045051 filed Sep. 28, 2022 International Search Report and Written Opinion dated Jan. 2, 2023.
PCT/US2022/047538 filed Oct. 24, 2022 International Search Report and Written Opinion dated Jan. 26, 2023.
U.S. Appl. No. 15/947,267, filed Apr. 6, 2018 Examiner's Answer dated Nov. 28, 2022.
U.S. Appl. No. 17/357,561, filed Jun. 24, 2021 Non-Final Office Action dated Aug. 11, 2022.
U.S. Appl. No. 17/357,561, filed Jun. 24, 2021 Notice of Allowance dated Dec. 9, 2022.
U.S. Appl. No. 17/371,993, filed Jul. 9, 2021 Notice of Allowance dated Nov. 3, 2022.
U.S. Appl. No. 17/392,002, filed Aug. 2, 2021, Non-Final Office Action dated Sep. 12, 2022.
U.S. Appl. No. 17/392,002, filed Aug. 2, 2021, Notice of Allowance dated Jan. 19, 2023.
Dziuda L et al: "Monitoring Respiration and Cardiac Activity Using Fiber Bragg Grating-Based Sensor", IEEE Transactions on Biomedical Engineering vol. 59, No. 7, Jul. 2012 pp. 1934-1942.
Dziuda L. et al: "Fiber-optic sensor for monitoring respiration and cardiac activity", 2011 IEEE Sensors Proceedings : Limerick, Ireland, Oct. 2011 pp. 413-416.
EP 20893677.3 filed Jun. 22, 2022 Extended European Search Report dated Oct. 13, 2023.
EP 20894633.5 filed Jun. 22, 2022 Extended European Search Report dated Oct. 16, 2023.
PCT/US2023/026581 filed Jun. 29, 2023 International Search Report and Written Opinion dated Oct. 27, 2023.
PCT/US2023/033471 filed Sep. 22, 2023 International Search Report and Written Opinion dated Dec. 21, 2023.
U.S. Appl. No. 16/984,104, filed Aug. 3, 2020 Notice of Allowance dated Nov. 21, 2023.
U.S. Appl. No. 17/500,678, filed Oct. 13, 2021 Advisory Action dated Dec. 7, 2023.
U.S. Appl. No. 17/500,678, filed Oct. 13, 2021 Non-Final Office Action dated Jan. 19, 2024.
U.S. Appl. No. 18/135,337, filed Apr. 17, 2023 Non-Final Office Action dated Dec. 22, 2023.
U.S. Appl. No. 17/569,350, filed Jan. 5, 2022 Non-Final Office Action dated Jan. 8, 2024.
PCT/US2018/026493 filed Apr. 6, 2018 International Search Report and Written Opinion dated Jun. 22, 2018.
PCT/US2020/044801 filed Aug. 3, 2020 International Search Report and Written Opinion dated Oct. 26, 2020.

(56) References Cited

OTHER PUBLICATIONS

PCT/US2020/062396 filed Nov. 25, 2020 International Preliminary Report on Patentability dated Jan. 29, 2021.
PCT/US2020/062396 filed Nov. 25, 2020 International Search Report and Written Opinion dated Mar. 2, 2021.
PCT/US2020/062407 filed Nov. 25, 2020 International Preliminary Report on Patentability dated Jan. 25, 2021.
PCT/US2020/062407 filed Nov. 25, 2020 International Search Report and Written Opinion dated Mar. 11, 2021.
PCT/US2021/038899 filed Jun. 24, 2021 International Search Report and Written Opinion dated Oct. 6, 2021.
PCT/US2021/038954 filed Jun. 24, 2021 International Search Report and Written Opinion dated Oct. 28, 2021.
PCT/US2021/041128 filed Jul. 9, 2021 International Search Report and Written Opinion dated Oct. 25, 2021.
PCT/US2021/044216 filed Aug. 2, 2021 International Search Report and Written Opinion dated Nov. 18, 2021.
PCT/US2021/054802 filed Oct. 13, 2021 International Search Report and Written Opinion dated Feb. 2, 2022.
PCT/US2022/011347 filed Jan. 5, 2022 International Search Report and Written Opinion dated May 3, 2022.
PCT/US2022/013897 filed Jan. 26, 2022 International Search Report and Written Opinion dated May 11, 2022.
U.S. Appl. No. 15/947,267, filed Apr. 6, 2018 Final Office Action dated Apr. 22, 2022.
U.S. Appl. No. 17/105,259, filed Nov. 25, 2020, Notice of Allowance dated Jul. 20, 2022.
U.S. Appl. No. 17/371,993, filed Jul. 9, 2021 Non-Final Office Action dated Jul. 12, 2022.
U.S. Appl. No. 15/947,267, filed Apr. 6, 2018 Final Office Action dated Jun. 30, 2021.
U.S. Appl. No. 15/947,267, filed Apr. 6, 2018 Final Office Action dated Nov. 10, 2020.
U.S. Appl. No. 15/947,267, filed Apr. 6, 2018 Non-Final Office Action dated Mar. 12, 2021.
U.S. Appl. No. 15/947,267, filed Apr. 6, 2018 Non-Final Office Action dated May 29, 2020.
U.S. Appl. No. 15/947,267, filed Apr. 6, 2018 Non-Final Office Action dated Oct. 13, 2021.
EP 20853352.1 filed Mar. 7, 2022 Extended European Search Report dated Jul. 27, 2023.
PCT/US2021/052046 filed Sep. 24, 2021 International Search Report and Written Opinion dated Jan. 11, 2022.
PCT/US2023/019239 filed Apr. 20, 2023 International Search Report and Written Opinion dated Jul. 20, 2023.
PCT/US2023/026487 filed Jun. 28, 2023 International Search Report and Written Opinion dated Sep. 6, 2023.
U.S. Appl. No. 16/984,104, filed Aug. 3, 2020 Final Office Action dated Sep. 21, 2023.
U.S. Appl. No. 16/984,104, filed Aug. 3, 2020 Non-Final Office Action dated Jun. 22, 2023.
U.S. Appl. No. 17/105,310, filed Nov. 25, 2020 Notice of Allowance dated Aug. 2, 2023.
U.S. Appl. No. 17/357,186, filed Jun. 24, 2021 Non Final Office Action dated May 30, 2023.
U.S. Appl. No. 17/357,186, filed Jun. 24, 2021 Notice of Allowance dated Aug. 23, 2023.
U.S. Appl. No. 17/484,960, filed Sep. 24, 2021 Non-Final Office Action dated Oct. 5, 2023.
U.S. Appl. No. 17/500,678, filed Oct. 13, 2021 Final Office Action dated Sep. 21, 2023.
Mayoral et al. Fiber Optic Sensors for Vital Signs Monitoring. A Review of Its Practicality in the Health Field. Biosensors (Basel). Feb. 23, 2021;11(2):58. doi: 10.3390/bios11020058.
U.S. Appl. No. 17/500,678, filed Oct. 13, 2021 Final Office Action dated Aug. 27, 2024.
U.S. Appl. No. 17/728,802, filed Apr. 25, 2022 Non-Final Office Action dated Aug. 28, 2024.
U.S. Appl. No. 17/747,903, filed May 18, 2022 Non-Final Office Action dated Aug. 15, 2024.
U.S. Appl. No. 17/853,590, filed Jun. 29, 2022 Non-Final Office Action dated Oct. 17, 2024.
U.S. Appl. No. 17/955,019, filed Sep. 28, 2022 Non-Final Office Action dated Sep. 27, 2024.
U.S. Appl. No. 18/132,623, filed Apr. 10, 2023, Final Office Action dated Sep. 6, 2024.
U.S. Appl. No. 18/538,111, filed Dec. 13, 2023 Non-Final Office Action dated Aug. 9, 2024.
U.S. Appl. No. 18/607,144, filed Mar. 15, 2024 Non-Final Office Action dated Sep. 24, 2024.
U.S. Appl. No. 17/569,350, filed Jan. 5, 2022 Non-Final Office Action dated Aug. 12, 2024.
P.J. de Feyter, P. Kay, C. Disco, P.W. Serruys, "Reference chart derived from post-stent-implantation intravascular ultrasound predictors of 6-month expected restenosis on quantitative coronary angiography." Circulation. vol. 100, No. 17 (Year: 1999).
PCT/US2023/026581 filed Jun. 29, 2023 International Preliminary Report on Patentability dated Dec. 18, 2024.
U.S. Appl. No. 17/500,678, filed Oct. 13, 2021 Advisory Action dated Nov. 6, 2024.
U.S. Appl. No. 17/500,678, filed Oct. 13, 2021 Non-Final Office Action dated Dec. 4, 2024.
U.S. Appl. No. 17/569,350, filed Jan. 5, 2022 Notice of Allowance dated Nov. 7, 2024.
U.S. Appl. No. 17/585,219, filed Jan. 26, 2022 Restriction Requirement dated Dec. 2, 2024.
U.S. Appl. No. 17/728,802, filed Apr. 25, 2022 Final Office Action dated Jan. 17, 2025.
U.S. Appl. No. 17/747,903, filed May 18, 2022 Final Office Action dated Jan. 27, 2025.
U.S. Appl. No. 17/955,019, filed Sep. 28, 2022 Final Office Action dated Feb. 4, 2025.
U.S. Appl. No. 17/971,873, filed Oct. 24, 2022 Non-Final Office Action dated Dec. 27, 2024.
U.S. Appl. No. 18/132,231, filed Apr. 7, 2023 Final Office Action dated Jan. 31, 2025.
U.S. Appl. No. 18/132,623, filed Apr. 10, 2023, Notice of Allowance dated Nov. 19, 2024.
U.S. Appl. No. 18/383,809, filed Oct. 25, 2023 Non-Final Office Action dated Dec. 16, 2024.
U.S. Appl. No. 18/538,111, filed Dec. 13, 2023 Final Office Action dated Feb. 4, 2025.
U.S. Appl. No. 17/585,219, filed Jan. 26, 2022 Non-Final Office Action dated Feb. 27, 2025.
U.S. Appl. No. 17/728,802, filed Apr. 25, 2022 Advisory Action dated Apr. 4, 2025.
U.S. Appl. No. 17/853,590, filed Jun. 29, 2022 Notice of Allowance dated Mar. 5, 2025.
U.S. Appl. No. 17/952,645, filed Sep. 26, 2022 Non-Final Office Action dated Feb. 28, 2025.
U.S. Appl. No. 18/132,231, filed Apr. 7, 2023 Notice of Allowance dated Apr. 10, 2025.
U.S. Appl. No. 18/607,144, filed Mar. 15, 2024 Final Office Action dated Feb. 19, 2025.

* cited by examiner

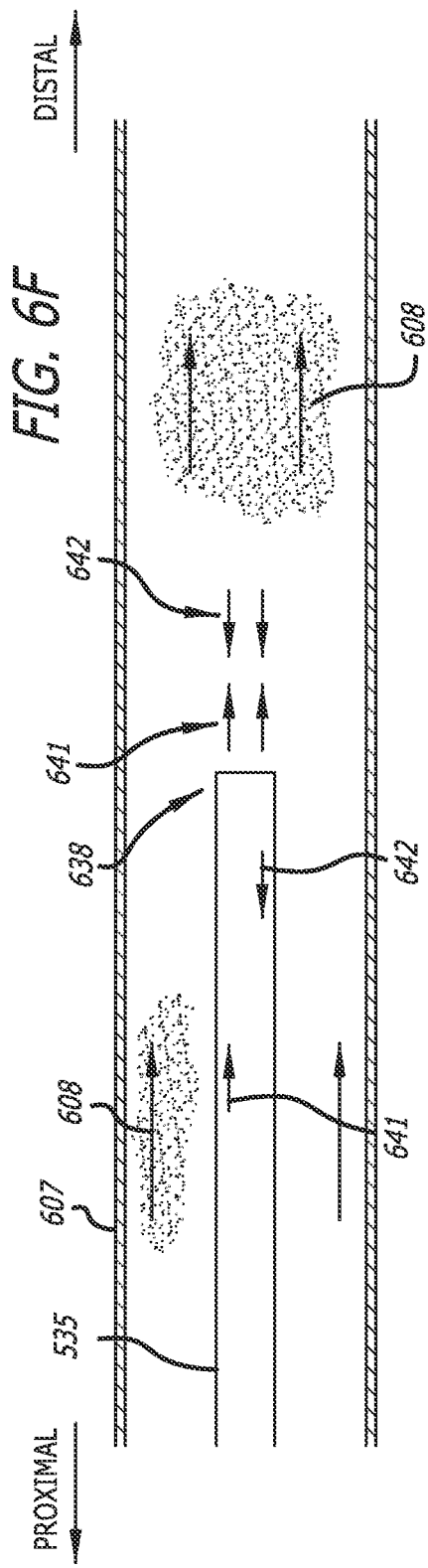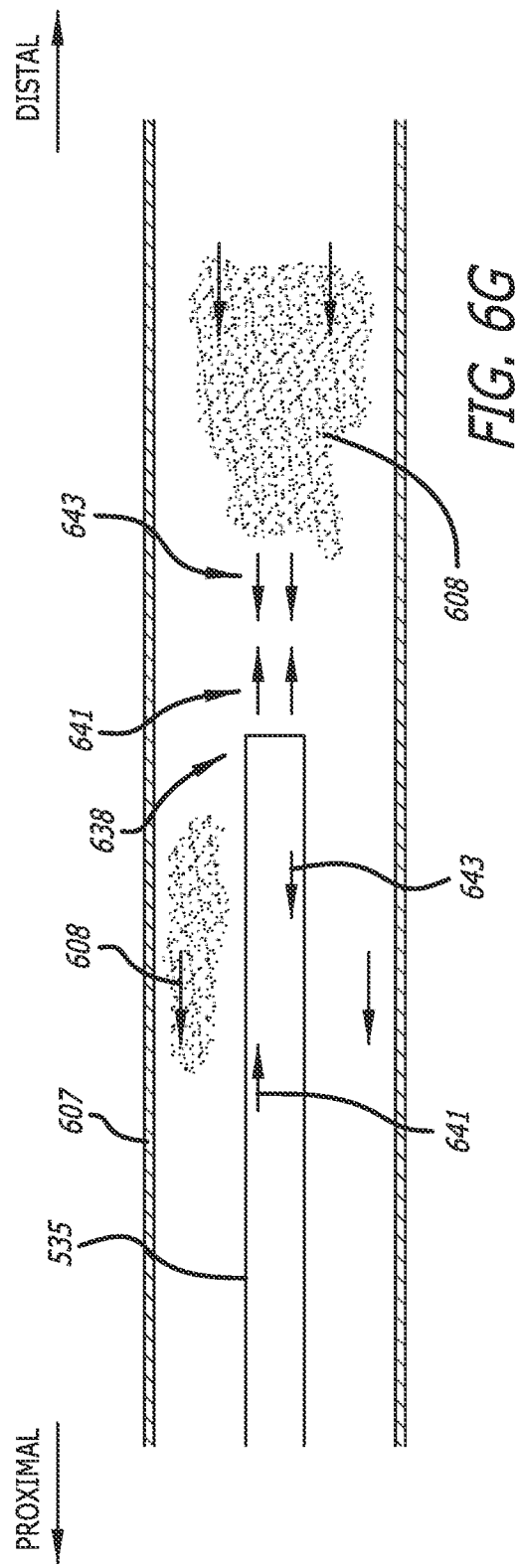

FIBER OPTIC MEDICAL SYSTEMS AND METHODS FOR IDENTIFYING BLOOD VESSELS

BACKGROUND

Elongate medical devices configured for insertion within a patient vasculature may be utilized to perform a myriad of treatments and diagnoses. One risk of performing vasculature procedures is inserting a vasculature device into the wrong blood vessel. In some instances, the wrong blood vessel may be an artery versus a vein or vice versa. As such, risk to the patient can be reduced by determining that the vasculature device is correctly inserted into a vein or an artery.

Disclosed herein are medical systems and methods that address the forgoing.

SUMMARY

Briefly summarized, disclosed herein is a medical system. According to some embodiments, the medical system includes an optical fiber configured for insertion within a blood vessel, where the optical fiber has one or more of core fibers extending along a longitudinal length of the optical fiber and a console operatively coupled with the optical fiber. The console includes a light source, an optical receiver, one or more processors, and a non-transitory computer-readable medium having stored thereon logic that, when executed by the one or more processors, causes operations of the system that include projecting a light distally along the optical fiber, the optical fiber inserted within the blood vessel; receiving at least one reflected light signal from the optical fiber; determining, based on the at least one reflected light signal, that the blood vessel is a vein or is an artery; and communicating a result of the determination to a user.

In some embodiments, the optical fiber is inserted within the blood vessel in a direction toward a heart of a patient, and the operations further include projecting a light defining a first wavelength distally away from a distal end of the optical fiber; receiving a reflected light signal having a second wavelength via the distal end; extracting from the reflected light signal a present wavelength shift between the first wavelength and the second wavelength; comparing the present wavelength shift with one or more wavelength shift limits stored in the non-transitory computer-readable medium; and determining, as result of the comparison, that the blood vessel is a vein or is an artery.

In some embodiments, each of the one or more core fibers includes a plurality of sensors distributed along the longitudinal length and each sensor of the plurality of sensors being configured to (i) reflect a light signal of a different spectral width based on received incident light, and (ii) change a characteristic of the reflected light signal based on a state of the optical fiber; and the at least one reflected light signal is generated by a sensor of the one or more core fibers.

In some embodiments, the state of the optical fiber includes a fluctuating movement of at least a portion of the optical fiber, and the operations further include extracting from the at least one reflected light signal present fluctuating movement data; comparing the present fluctuating movement data with a fluctuating movement limit stored in the non-transitory computer-readable medium; and determining, as result of the comparison, that the blood vessel is a vein or is an artery.

In some embodiments, the state of the optical fiber includes a compressive strain of the optical fiber caused by engagement of the optical fiber with one or more check valves of the blood vessel during insertion of the optical fiber, and the operations further include extracting from the at least one reflected light signal present compressive strain data; comparing the present compressive strain data with a compressive strain limit stored in the non-transitory computer-readable medium; and determining, as result of the comparison, that the blood vessel is a vein or is an artery.

In some embodiments, the state of the optical fiber includes pressure fluctuations exerted on the optical fiber, and the operations further include extracting from the at least one reflected light signal present pressure fluctuation data; comparing the present pressure fluctuation data with a pressure fluctuation limit stored in the non-transitory computer-readable medium; and determining, as result of the comparison, that the blood vessel is a vein or is an artery.

In some embodiments, the state of the optical fiber includes pressure fluctuations exerted on the optical fiber along an inserted length of the optical fiber, the pressure fluctuations caused by a pressure wave traveling longitudinally along the optical fiber, and the operations further include receiving a plurality of reflected light signals generated from a plurality of sensors disposed along the inserted length, where each reflected light signal is based on a pressure exerted on the optical fiber adjacent the respective sensor; extracting from the plurality of reflected light signals present pressure wave data; comparing the pressure wave data with one or more pressure wave limits stored in the non-transitory computer-readable medium; and determining, as result of the comparison, that the blood vessel is a vein or is an artery.

In some embodiments, the state of the optical fiber includes a pressure gradient exerted on the optical fiber along an inserted length of the optical fiber, and the operations further include receiving a plurality of reflected light signals generated from a plurality of sensors disposed along the inserted length, where each reflected light signal is based on a pressure exerted on the optical fiber adjacent the respective sensor; extracting from the plurality of reflected light signals a present pressure gradient data; comparing the pressure gradient data with a pressure gradient limit stored in the non-transitory computer-readable medium; and determining, as result of the comparison, that the blood vessel is a vein or is an artery.

In some embodiments, the optical fiber is inserted within the blood vessel in a direction toward a heart of a patient, the optical fiber is inserted within a lumen of a catheter, and the catheter is delivering an infusate to the blood vessel. The state of the optical fiber includes a first temperature experienced by a first section of the optical fiber disposed within the catheter and a second temperature experienced by a second section of the optical fiber extending distally beyond a distal end of the catheter. The operations further include receiving a first reflected light signal from a sensor disposed along the first section, the first reflected light signal based on a first temperature; receiving a second reflected light signal from a sensor disposed along the second section, the second reflected light signal based a second temperature; extracting from the first and second reflected light signals a present temperature difference data between the first and second temperatures; comparing the present temperature difference data with a temperature difference limit stored in the non-transitory computer-readable medium; and determining, as result of the comparison, that the blood vessel is a vein or is an artery.

In some embodiments, the optical fiber is inserted within the blood vessel in a direction toward a heart of a patient, the optical fiber extends along a catheter, and the catheter is configured to deliver an infusate to the blood vessel. The state of the optical fiber includes a first temperature experienced by a section of the optical fiber extending beyond a distal end of the catheter during non-delivery of the infusate and a second temperature experienced by the section during delivery of the infusate. The operations further include receiving a first reflected light signal from a sensor disposed along the section during non-delivery of the infusate, where the first reflected light signal is based on the first temperature; receiving a second reflected light signal from the sensor, where the second reflected light signal is based on the second temperature; extracting from the first and second reflected light signals present temperature difference data between the first and second temperatures; comparing the present temperature difference data with a temperature difference limit stored in the non-transitory computer-readable medium; and determining, as result of the comparison, that the blood vessel is a vein or is an artery.

In some embodiments, the optical fiber is coupled with an elongate medical device, where the elongate medical device includes a catheter, a stylet, a probe, or a guidewire.

Also further summarized herein is a method performed by a medical system of identifying a blood vessel that, according to some embodiments, includes projecting incident light distally along an optical fiber of the system, where the optical fiber is disposed within a blood vessel; receiving at least one reflected light signal from the optical fiber; and identifying the blood vessel as a vein or as an artery based on the at least one reflected light signal.

In some embodiments, the method further includes projecting the incident light distally away from the distal end of the optical fiber, where the incident light has a defined wavelength; receiving a reflected light signal emanating from particles within the blood via the optical fiber; determining a wavelength shift between the incident light and the reflected light signal; and identifying the blood vessel as a vein or as an artery based on the wavelength shift.

In some embodiments of the method, the optical fiber includes a number of core fibers, where at least one of the fiber cores includes a plurality of sensors distributed along a longitudinal length of the optical fiber, and where each sensor of the plurality of sensors is configured to (i) reflect a light signal of a different spectral width based on received incident light, and (ii) change a characteristic of the reflected light signal based on a state of the optical fiber. In such an embodiment, the at least one reflected light signal is generated by a sensor of the optical fiber.

In some embodiments of the method, the state of the optical fiber includes a fluctuating movement of at least a portion of the optical fiber, and the method further includes extracting from the at least one reflected light signal present fluctuating movement data and identifying the blood vessel as a vein or as an artery based on the present fluctuating movement data.

In some embodiments of the method, the state of the optical fiber includes a compressive strain of the optical fiber caused by engagement of the optical fiber with one or more check valves of the blood vessel during advancement of the optical fiber along the blood vessel, and the method further includes extracting from the at least one reflected light signal present compressive strain data and identifying the blood vessel as a vein or as an artery based on the present compressive strain data.

In some embodiments of the method, the state of the optical fiber includes a pressure fluctuations exerted on the optical fiber, and the method further includes extracting from the at least one reflected light signal present pressure fluctuation data; identifying the blood vessel as a vein or as an artery based on the present pressure fluctuation data.

In some embodiments of the method, the state of the optical fiber includes pressure fluctuations exerted on the optical fiber along a length of the optical fiber disposed within the blood vessel, where the pressure fluctuations are caused by a pressure wave traveling longitudinally along the optical fiber, and the method further includes receiving a plurality of reflected light signals generated from a plurality of sensors disposed along the length of the optical fiber disposed within the blood vessel, where each reflected light signal is based on a pressure exerted on the optical fiber adjacent the respective sensor; extracting from the plurality of reflected light signals present pressure wave data; and identifying the blood vessel as a vein or as an artery based on the present pressure wave data.

In some embodiments of the method, the state of the optical fiber includes a pressure gradient exerted on the optical fiber along a length of the optical fiber disposed within the blood vessel, and the method further includes receiving a plurality of reflected light signals generated from a plurality of sensors disposed along the length of the optical fiber disposed within the blood vessel, where each reflected light signal is based on a pressure exerted on the optical fiber adjacent the respective sensor; extracting from the plurality of reflected light signals present pressure gradient data; and identifying the blood vessel as a vein or as an artery based on the present pressure gradient data.

In some embodiments of the method, the optical fiber is inserted within the blood vessel in a direction toward a heart of a patient, the optical fiber is inserted within a lumen of a catheter, and the catheter is delivering an infusate to the blood vessel. The state of the optical fiber includes a first temperature experienced by a first section of the optical fiber disposed within the catheter and a second temperature experienced by a second section of the optical fiber extending distally beyond a distal end of the catheter. In such embodiments, the method further includes receiving a first reflected light signal from a sensor disposed along the first section, where the first reflected light signal is based on the first temperature; receiving a second reflected light signal from a sensor disposed along the second section, where the second reflected light signal is based on the second temperature; extracting from the first and second reflected light signals present temperature difference data between the first and second temperatures; and identifying the blood vessel as a vein or as an artery based on the present temperature difference data.

In some embodiments of the method, the optical fiber is inserted within the blood vessel in a direction toward a heart of a patient, the optical fiber is inserted within a lumen of a catheter, where the catheter is configured to deliver an infusate to the blood vessel, and the state of the optical fiber includes a first temperature experienced by a section of the optical fiber extending beyond a distal end of the catheter during non-delivery of the infusate and a second temperature experienced by the section during delivery of the infusate. In such embodiments, the method further includes receiving a first reflected light signal from a sensor disposed along the section during non-delivery of the infusate, where the first reflected light signal is based on the first temperature; receiving a second reflected light signal from the sensor, where the second reflected light signal is based on the second temperature; extracting from the first and second reflected light signals present temperature difference data between the first and second temperatures; and identifying the blood vessel as a vein or as an artery based on the present temperature difference data.

In some embodiments of the method, the optical fiber is coupled with an elongate medical device, where the elongate medical device includes a catheter, a stylet, a probe, or a guidewire.

These and other features of the concepts provided herein will become more apparent to those of skill in the art in view of the accompanying drawings and following description, which disclose particular embodiments of such concepts in greater detail.

BRIEF DESCRIPTION OF THE DRAWINGS

Embodiments of the disclosure are illustrated by way of example and not by way of limitation in the figures of the accompanying drawings, in which like references indicate similar elements and in which:

FIGS. 6F-6G illustrate an implementation of the of optical fiber of FIG. 5 identifying a blood vessel based a wavelength shift between a light projected onto and a light reflected off of particles within the blood, in accordance with some embodiments.

DETAILED DESCRIPTION

Figure 1:
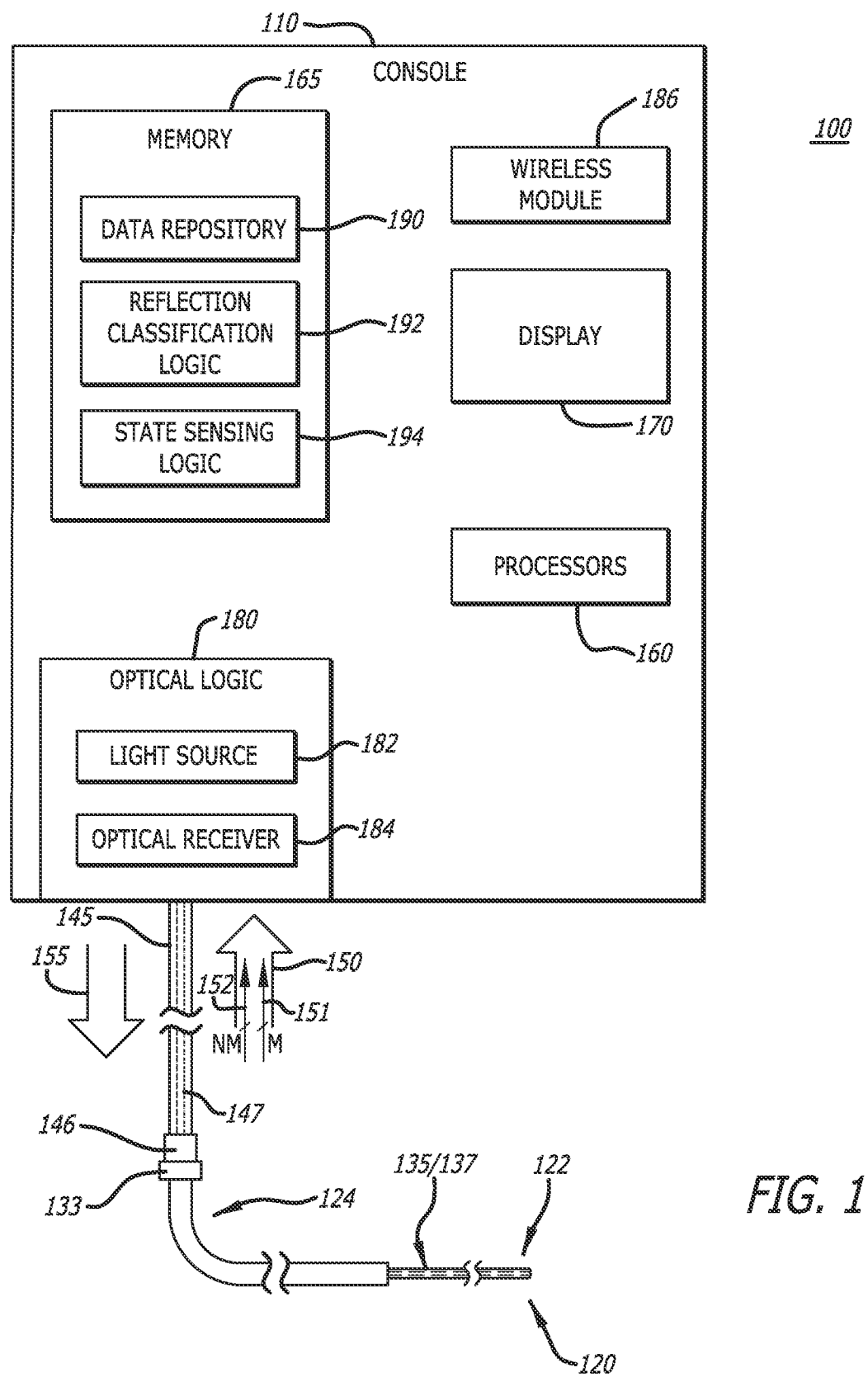
FIG. 1 is an illustrative embodiment of a medical system including an elongate probe having an optical fiber, in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including an optical fiber disclosed herein. As used herein, the proximal portion of an optical fiber is the portion nearest a practitioner during use or least inserted within a patient, while the distal portion is the portion at the opposite end. For example, the proximal end of the optical fiber is defined as the end closest to the practitioner during utilization of the optical fiber. The distal end is the end opposite the proximal end, along the longitudinal direction of the optical fiber, e.g., the end furthest inserted into the patient.

The term "logic" may be representative of hardware, firmware or software that is configured to perform one or more functions. As hardware, the term logic may refer to or include circuitry having data processing and/or storage functionality. Examples of such circuitry may include, but are not limited or restricted to a hardware processor (e.g., microprocessor, one or more processor cores, a digital signal processor, a programmable gate array, a microcontroller, an application specific integrated circuit (ASIC), etc.), a semiconductor memory, or combinatorial elements.

Additionally, or in the alternative, the term logic may refer to or include software such as one or more processes, one or more instances, Application Programming Interface(s) (API), subroutine(s), function(s), applet(s), servlet(s), routine(s), source code, object code, shared library/dynamic link library (dll), or even one or more instructions. This software may be stored in any type of a suitable non-transitory storage medium, or transitory storage medium (e.g., electrical, optical, acoustical or other form of propagated signals such as carrier waves, infrared signals, or digital signals). Examples of a non-transitory storage medium may include, but are not limited or restricted to a programmable circuit; non-persistent storage such as volatile memory (e.g., any type of random-access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the logic may be stored in persistent storage.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations may be made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially straight" is recited with respect to a feature, it is understood that in further embodiments, the feature can have a precisely straight configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

FIG. 1 illustrates an embodiment of a medical system including a medical device. As shown, the medical system (system) 100 generally includes a console 110 and an elongate probe 120 communicatively coupled with the console 110. The elongate probe 120 defines a distal end 122 and includes a console connector 133 at a proximal end 124. The elongate probe 120 includes an optical fiber 135 including multiple core fibers extending along a length of the elongate probe 120 as further described below. The console connector 133 enables the elongate probe 120 to be operably connected to the console 110 via an interconnect 145 including one or more optical fibers 147 (hereinafter, "optical fiber(s)"). Herein, the connector 146 is configured to engage (mate) with the console connector 133 to allow for the propagation of light between the console 110.

The elongate probe 120 may be configured to perform any of a variety of medical procedures. As such, the elongate probe 120 may be a component of or employed with a variety of medical instruments/devices 119. In some implementations, the elongate probe 120 may take the form of a guidewire, a stylet, or a catheter, for example. The elongate probe 120 may be formed of a metal, a plastic or a combination thereof. In some embodiments, the elongate probe 120 may include a lumen extending therealong having an optical fiber 135 disposed therein.

In some implementations, the elongate probe 120 may be integrated into a vascular catheter. Other exemplary implementations include drainage catheters, surgery devices, stent insertion and/or removal devices, biopsy devices, endoscopes, and kidney stone removal devices. In short, the elongate probe 120 may be employed with, or the elongate probe 120 may be a component of, any medical device 119 that is inserted into a patient.

According to one embodiment, the console 110 includes one or more processors 160, a memory 165, a display 170, and optical logic 180, although it is appreciated that the console 110 can take one of a variety of forms and may include additional components (e.g., power supplies, ports, interfaces, etc.) that are not directed to aspects of the disclosure. An illustrative example of the console 110 is illustrated in U.S. Publication No. 2019/0237902, the entire contents of which are incorporated by reference herein. The one or more processors 160, with access to the memory 165 (e.g., non-volatile memory or non-transitory, computer-readable medium), are included to control functionality of the console 110 during operation. As shown, the display 170 may be a liquid crystal diode (LCD) display integrated into the console 110 and employed as a user interface to display information to the clinician, especially during an instrument placement procedure. In another embodiment, the display 170 may be separate from the console 110. Although not shown, a user interface is configured to provide user control of the console 110.

Referring still to FIG. 1, the optical logic 180 is configured to support operability of the elongate probe 120 and enable the return of information to the console 110, which may be used to determine the physical state associated with the elongate probe 120 along or an image of the patient body. The physical state of the elongate probe 120 may be based on changes in characteristics of the reflected light signals 150 received at the console 110 from the elongate probe 120. The characteristics may include shifts in wavelength caused by strain on certain regions of the core fibers integrated within the optical fiber 135 positioned within or operating as the elongate probe 120, as shown below. As discussed herein, the optical fiber 135 may be comprised of a number (e.g., 1, 2, 3, 4, or more) of core fibers $137_1$-$137_M$ (M=1 for a single core, and M>2 for a multi-core), where the core fibers $137_1$-$137_M$ may collectively be referred to as core fiber(s) 137. Unless otherwise specified or the instant embodiment requires an alternative interpretation, embodiments discussed herein will refer to an optical fiber 135. From information associated with the reflected light signals 150, the console 110 may determine (through computation or extrapolation of the wavelength shifts) the physical state of the elongate probe 120 and/or physical conditions experienced by the probe 120, such as strain, temperature, pressure, or movement, for example.

According to one embodiment of the disclosure, as shown in FIG. 1, the optical logic 180 may include a light source 182 and an optical receiver 184. The light source 182 is configured to transmit the incident light 155 (e.g., broadband) for propagation over the optical fiber(s) 147 included in the interconnect 145, which are optically connected to the optical fiber 135 within the elongate probe 120. In one embodiment, the light source 182 is a tunable swept laser, although other suitable light sources can also be employed in addition to a laser, including semi-coherent light sources, LED light sources, etc.

The optical receiver 184 is configured to: (i) receive returned optical signals, namely reflected light signals 150 received from optical fiber-based reflective gratings (sensors) fabricated within each core fiber of the optical fiber 135 deployed within the elongate probe 120, and (ii) translate the reflected light signals 150 into reflection data (from a data repository 190), namely data in the form of electrical signals representative of the reflected light signals including wavelength shifts caused by strain. The reflected light signals 150 associated with different spectral widths may include reflected light signals 151 provided from sensors positioned in the center core fiber (reference) of the optical fiber 135 and/or reflected light signals 152 provided from sensors positioned in the periphery core fibers of the optical fiber 135, as described below. Herein, the optical receiver 184 may be implemented as a photodetector, such as a positive-intrinsic-negative "PIN" photodiode, avalanche photodiode, or the like.

As shown, both the light source 182 and the optical receiver 184 are operably connected to the one or more processors 160, which governs their operation. Also, the optical receiver 184 is operably coupled so as to provide the reflection data (from the data repository 190) to the memory 165 for storage and processing by reflection data classification logic 192. The reflection data classification logic 192 may be configured to: (i) identify which core fibers pertain to which of the received reflection data (from the data repository 190) and (ii) segregate the reflection data stored within the data repository 190 provided from reflected light signals 150 pertaining to similar regions of the elongate probe 120 or spectral widths into analysis groups. The reflection data for each analysis group is made available to state sensing logic 194 for analytics.

According to one embodiment of the disclosure, the state sensing logic 194 is configured to compare wavelength shifts measured by sensors deployed in each periphery core fiber at the same measurement region of the elongate probe 120 (or same spectral width) to the wavelength shift at a center core fiber of the optical fiber 135 positioned along central axis and operating as a neutral axis of bending. From these analytics, the state sensing logic 194 may determine the shape the core fibers have taken in three-dimensional space and may further determine the current physical state of the elongate probe 120 in three-dimensional space for rendering on the display 170.

According to one embodiment of the disclosure, the state sensing logic 194 may generate a rendering of the current physical state of the elongate probe 120, based on heuristics or run-time analytics. For example, the state sensing logic 194 may be configured in accordance with machine-learning techniques to access the data repository 190 with pre-stored data (e.g., images, etc.) pertaining to different regions of the elongate probe 120 in which reflected light from core fibers have previously experienced similar or identical wavelength shifts. From the pre-stored data, the current physical state of the elongate probe 120 may be rendered. Alternatively, as another example, the state sensing logic 194 may be configured to determine, during run-time, changes in the physical state of each region of the optical fiber 135 based on at least: (i) resultant wavelength shifts experienced by different core fibers within the optical fiber 135, and (ii) the relationship of these wavelength shifts generated by sensors positioned along different periphery core fibers at the same cross-sectional region of the optical fiber 135 to the wavelength shift generated by a sensor of the center core fiber at the same cross-sectional region. It is contemplated that other processes and procedures may be performed to utilize the wavelength shifts as measured by sensors along each of the core fibers within the optical fiber 135 to render appropriate changes in the physical state of the elongate probe 120, especially to enable guidance of the elongate probe 120 when positioned within the patient and at a desired destination within the body.

It is contemplated that other processes and procedures may be performed to utilize the wavelength shifts as measured by sensors along each of the core fibers within the optical fiber 135 to render appropriate changes in the physical state of the probe 120, especially to enable guidance of the probe 120 when positioned within the patient and at a desired destination within the body. For example, wavelength shifts as measured by sensors along one or more of the core fibers may be based on physical states or condition of the probe 120 other than or in addition to longitudinal strain experienced by the elongate probe 120. Alternative or additional physical states may include one or more of torsional strain, temperature, motion, oscillations, pressure, or fluid flow adjacent the elongate probe.

Figure 2:
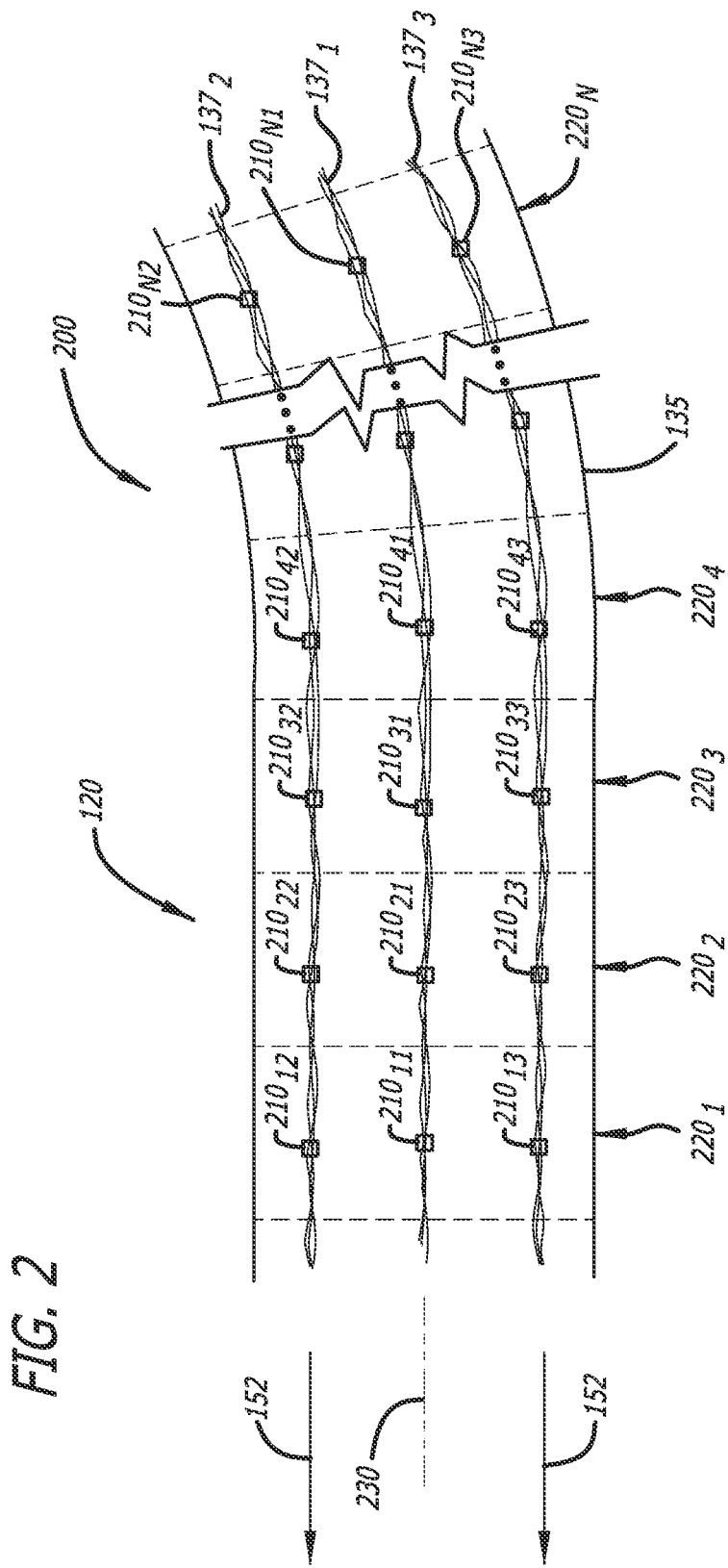
FIG. 2 is an exemplary embodiment of a structure of a section of the elongate probe of FIG. 1, in accordance with some embodiments.

Referring to FIG. 2, an exemplary embodiment of a structure of a section of the optical fiber of FIG. 1 is shown in accordance with some embodiments. The optical fiber section 200 of the optical fiber 135 depicts certain core fibers $137_1$-$137_M$ (M>2, M=4 as shown, see FIG. 3A) along with the spatial relationship between sensors (e.g., reflective gratings) $210_{11}$-$210_{NM}$ (N>2; M>2) present within the core fibers $137_1$-$137_M$, respectively. As noted above, the core fibers $137_1$-$137_M$ may be collectively referred to as "the core fibers 137."

As shown, the section 200 is subdivided into a plurality of cross-sectional regions $220_1$-$220_N$, where each cross-sectional region $220_1$-$220_N$ corresponds to reflective gratings $210_{11}$-$210_{14}$ . . . $210_{N1}$-$210_{N4}$. Some or all of the cross-sectional regions $220_1$ . . . $220_N$ may be static (e.g., prescribed length) or may be dynamic (e.g., vary in size among the regions $220_1$ . . . $220_N$). A first core fiber $137_1$ is positioned substantially along a center (neutral) axis 230 while core fiber $137_2$ may be oriented within the cladding of the optical fiber 135, from a cross-sectional, front-facing perspective, to be position on "top" the first core fiber $137_1$. In this deployment, the core fibers $137_3$ and $137_4$ may be positioned "bottom left" and "bottom right" of the first core fiber $137_1$. As examples, FIGS. 3A-4B provides illustrations of such.

Referencing the first core fiber $137_1$ as an illustrative example, when the elongate probe 120 (see FIG. 1) is operative, each of the reflective gratings $210_1$-$210_N$ reflects light for a different spectral width. As shown, each of the gratings $210_{1i}$-$210_{Ni}$ (1≤i≤M) is associated with a different, specific spectral width, which would be represented by different center frequencies of $f_1$ . . . $f_N$, where neighboring spectral widths reflected by neighboring gratings are non-overlapping according to one embodiment of the disclosure.

Herein, positioned in different core fibers $137_2$-$137_3$ but along at the same cross-sectional regions 220-$220_N$ of the optical fiber 135, the gratings $210_{12}$-$210_{N2}$ and $210_{13}$-$210_{N3}$ are configured to reflect incoming light at the same (or substantially similar) center frequency. As a result, the reflected light returns information that allows for a determination of the physical state of the core fibers 137 (and the elongate probe 120) based on wavelength shifts measured from the returned, reflected light about the center frequency. In particular, strain (e.g., compression or tension) applied to the optical fiber 135 (e.g., at least core fibers $137_2$-$137_3$) results in wavelength shifts associated with the returned, reflected light. Based on different locations, the core fibers $137_1$-$137_4$ experience different types and/or degrees of strain based on angular path changes as the elongate probe 120 advances in the patient.

For example, with respect to the multi-core optical fiber section 200 of FIG. 2, in response to angular (e.g., radial) movement of the elongate probe 120 is in the left-veering direction, the fourth core fiber $137_4$ (see FIG. 3A) of the optical fiber 135 with the shortest radius during movement (e.g., core fiber closest to a direction of angular change) would exhibit compression (e.g., forces to shorten length). At the same time, the third core fiber $137_3$ with the longest radius during movement (e.g., core fiber furthest from the direction of angular change) would exhibit tension (e.g., forces to increase length). As these forces are different and unequal, the reflected light from reflective gratings $210_{N2}$ and $210_{N3}$ associated with the core fiber $137_2$ and $137_3$ will exhibit different changes in wavelength. The differences in wavelength shift of the reflected light signals 150 can be used to extrapolate the physical configuration of the elongate probe 120 by determining the degrees of wavelength change caused by compression/tension for each of the periphery fibers (e.g., the second core fiber $137_2$ and the third core fiber $137_3$) in comparison to the wavelength of the reference core fiber (e.g., first core fiber $137_1$) located along the neutral axis 230 of the optical fiber 135. These degrees of wavelength change may be used to extrapolate the physical state of the elongate probe 120. The reflected light signals 150 are reflected back to the console 110 via individual paths over a particular core fiber $137_1$-$137_M$.

Figure 3A:
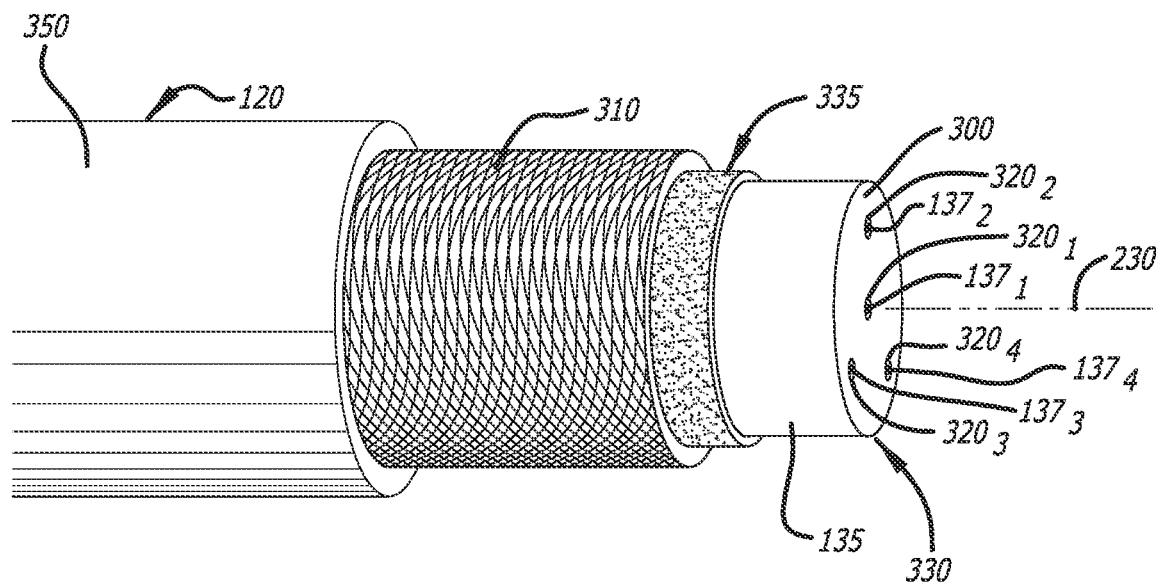
FIG. 3A illustrates an embodiment of the probe of FIG. 1, in accordance with some embodiments.

Referring to FIG. 3A, a first exemplary embodiment of the probe of FIG. 1 supporting both an optical and electrical signaling is shown in accordance with some embodiments. Herein, the probe 120 features a centrally located multi-core optical fiber 135, which includes a cladding 300 and a plurality of core fibers $137_1$-$137_M$ (M>2; M=4) residing within a corresponding plurality of lumens $320_1$-$320_M$. While the multi-core optical fiber 135 is illustrated within four (4) core fibers $137_1$-$137_4$, a greater number of core fibers $137_1$-$137_M$ (M>4) may be deployed to provide a more detailed three-dimensional sensing of the physical state (e.g., shape, etc.) of the multi-core optical fiber 135 and the probe 120 deploying the optical fiber 135.

In some embodiments, the multi-core optical fiber 135 is encapsulated within a concentric braided tubing 310 positioned over a low coefficient of friction layer 335. The braided tubing 310 may feature a "mesh" construction, in which the spacing between the intersecting conductive elements is selected based on the degree of rigidity desired for the probe 120, as a greater spacing may provide a lesser rigidity, and thereby, a more pliable probe 120.

Figure 3B:
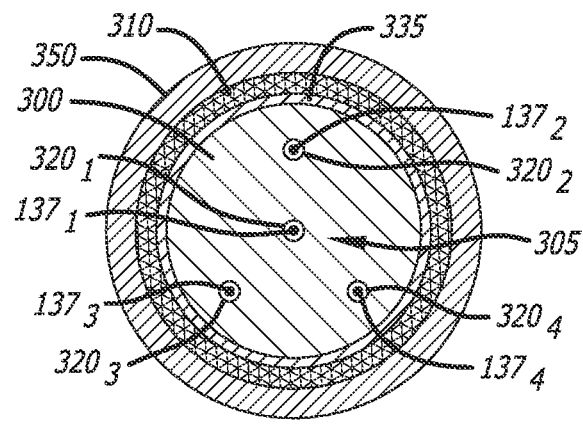
FIG. 3B is a cross sectional end view of the probe of FIG. 3A, in accordance with some embodiments.

According to this embodiment of the disclosure, as shown in FIGS. 3A-3B, the core fibers $137_1$-$137_4$ include (i) a central core fiber $137_1$ and (ii) a plurality of periphery core fibers $137_1$-$137_4$, which are maintained within lumens $320_1$-$320_4$ formed in the cladding 300. According to one embodiment of the disclosure, one or more of the lumen $320_1$-$320_4$ may be configured with a diameter sized to be greater than the diameter of the core fibers $137_1$-$137_4$. By avoiding a majority of the surface area of the core fibers $137_1$-$137_4$ from being in direct physical contact with a wall surface of the lumens $320_1$-$320_4$, the wavelength changes to the incident light are caused by angular deviations in the multi-core optical fiber 135 thereby reducing influence of compression and tension forces being applied to the walls of the lumens $320_1$-$320_M$, not the core fibers $137_1$-$137_M$ themselves.

As further shown in FIGS. 3A-3B, the core fibers $137_1$-$137_4$ may include central core fiber $137_1$ residing within a first lumen $320_1$ formed along the first neutral axis 230 and a plurality of core fibers $137_2$-$137_4$ residing within lumens $320_1$-$320_4$ each formed within different areas of the cladding 300 radiating from the first neutral axis 230. In general, the core fibers $137_1$-$137_4$, exclusive of the central core fiber $137_1$, may be positioned at different areas within a cross-sectional area 305 of the cladding 300 to provide sufficient separation to enable three-dimensional sensing of the multi-core optical fiber 135 based on changes in wavelength of incident light propagating through the core fibers $137_1$-$137_4$ and reflected back to the console for analysis.

For example, where the cladding 300 features a circular cross-sectional area 305 as shown in FIG. 3B, the core fibers $137_1$-$137_4$ may be positioned substantially equidistant from each other as measured along a perimeter of the cladding 300, such as at "top" (12 o'clock), "bottom-left" (8 o'clock) and "bottom-right" (4 o'clock) locations as shown. Hence, in general terms, the core fibers $137_1$-$137_4$ may be positioned within different segments of the cross-sectional area 305. Where the cross-sectional area 305 of the cladding 300 has a distal tip 330 and features a polygon cross-sectional shape (e.g., triangular, square, rectangular, pentagon, hexagon, octagon, etc.), the central core fiber $137_1$ may be located at or near a center of the polygon shape, while the remaining core fibers $137_2$-$137_M$ may be located proximate to angles between intersecting sides of the polygon shape.

Referring still to FIGS. 3A-3B, operating as the conductive medium for the probe 120, the braided tubing 310 may provide mechanical integrity to the multi-core optical fiber 135 and may also operate as a conductive pathway for electrical signals. The cladding 300 and the braided tubing 310, which is positioned concentrically surrounding a circumference of the cladding 300, are contained within the same insulating layer 350. The insulating layer 350 may be a sheath or conduit made of protective, insulating (e.g., non-conductive) material that encapsulates both for the cladding 300 and the braided tubing 310, as shown.

Figure 4A:
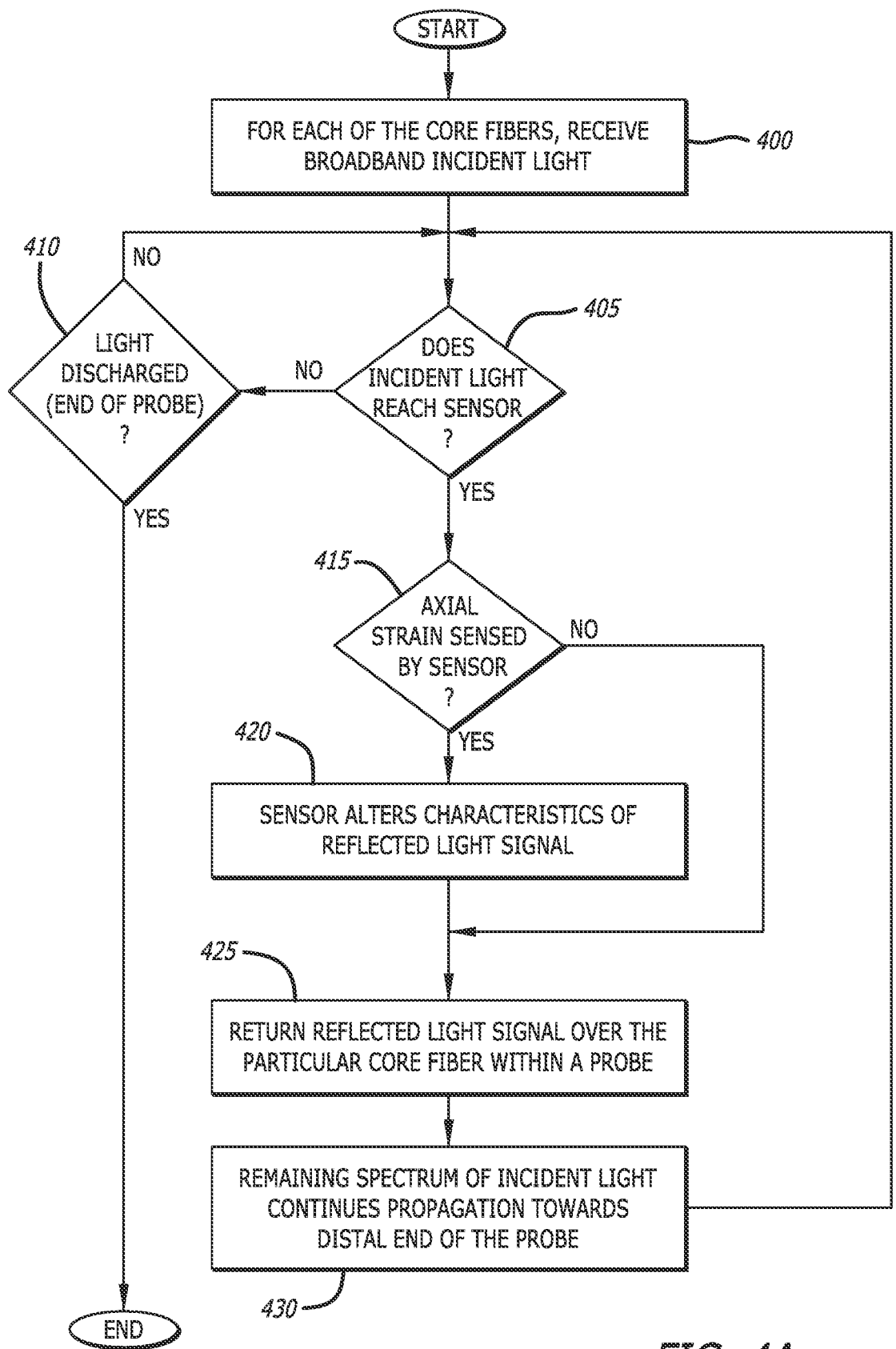
FIGS. 4A-4B are flowcharts of the methods of operations conducted by the medical system of FIG. 1 to achieve optic three-dimensional shape sensing, in accordance with some embodiments.
Figure 4B:
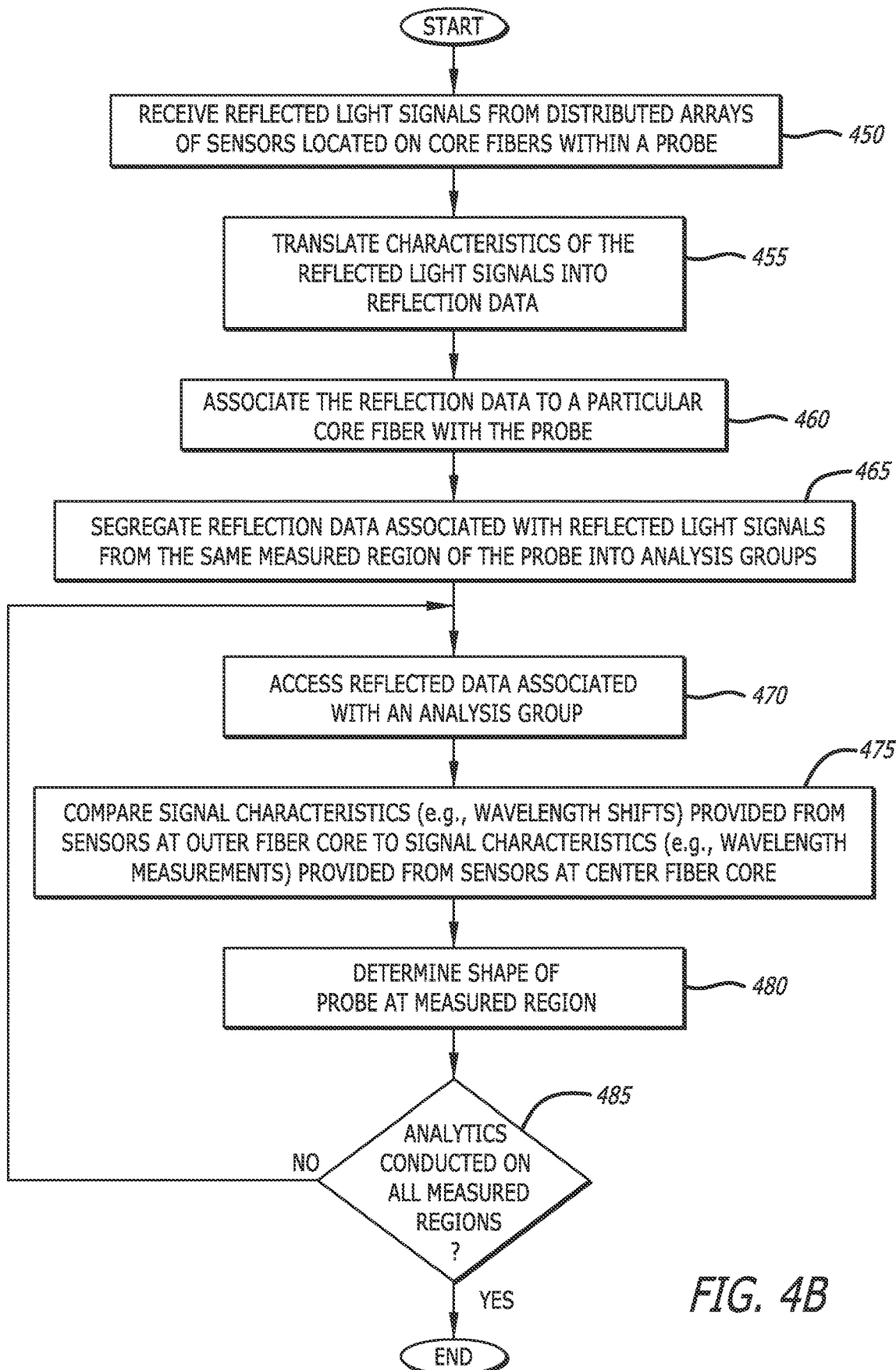

Referring to FIGS. 4A-4B, flowcharts of methods of operations conducted by the medical device system of FIG. 1 to achieve optic three-dimensional shape sensing are shown in accordance with some embodiments. The first micro-lumen is coaxial with the central axis of the probe. The first micro-lumen is configured to retain a center core fiber. Two or more micro-lumen, other than the first micro-lumen, are positioned at different locations circumferentially spaced along the circumferential edge of the probe. For example, two or more of the second plurality of micro-lumens may be positioned at different quadrants along the circumference edge of the probe.

Furthermore, each core fiber includes a plurality of sensors spatially distributed along its length between at least the proximal and distal ends of the probe. This array of sensors is distributed to position sensors at different regions of the core fiber to enable distributed measurements of strain throughout the entire length or a selected portion of the probe. These distributed measurements may be conveyed through reflected light of different spectral widths (e.g., specific wavelength or specific wavelength ranges) that undergoes certain wavelength shifts based on the type and degree of strain, including oscillations of the strain.

According to one embodiment of the disclosure, as shown in FIG. 4A, for each core fiber, broadband incident light is supplied to propagate through a particular core fiber (block 400). Unless discharged, upon the incident light reaching a sensor of a distributed array of sensors measuring strain on a particular core fiber, light of a prescribed spectral width associated with the first sensor is to be reflected back to an optical receiver within a console (blocks 405-410). Herein, the sensor alters characteristics of the reflected light signal to identify the type and degree of strain on the particular core fiber as measured by the first sensor (blocks 415-420). According to one embodiment of the disclosure, the alteration in characteristics of the reflected light signal may signify a change (shift) in the wavelength of the reflected light signal from the wavelength of the incident light signal associated with the prescribed spectral width. The sensor returns the reflected light signal over the core fiber and the remaining spectrum of the incident light continues propagation through the core fiber toward a distal end of the probe (blocks 425-430). The remaining spectrum of the incident light may encounter other sensors of the distributed array of sensors, where each of these sensors would operate as set forth in blocks 405-430 until the last sensor of the distributed array of sensors returns the reflected light signal associated with its assigned spectral width and the remaining spectrum is discharged as illumination.

Referring now to FIG. 4B, during operation, multiple reflected light signals are returned to the console from each of the plurality of core fibers residing within the corresponding plurality of micro-lumens formed within a probe. In particular, the optical receiver receives reflected light signals from the distributed arrays of sensors located on the center core fiber and the outer core fibers and translates the reflected light signals into reflection data, namely electrical signals representative of the reflected light signals including wavelength shifts caused by strain (blocks 450-455). The reflection data classification logic is configured to identify which core fibers pertain to which reflection data and segregate reflection data provided from reflected light signals pertaining to a particular measurement region (or similar spectral width) into analysis groups (block 460-465).

Each analysis group of reflection data is provided to sensing logic for analytics (block 470). Herein, the sensing logic compares wavelength shifts at each outer core fiber with the wavelength shift at the center core fiber positioned along central axis and operating as a neutral axis of bending (block 475). From this analytics, on all analytic groups (e.g., reflected light signals from sensors in all or most of the core fibers), the sensing logic may determine the shape the core fibers have taken in three-dimensional space, from which the sensing logic can determine the current physical state of the probe in three-dimensional space (blocks 480-485).

Figure 5:
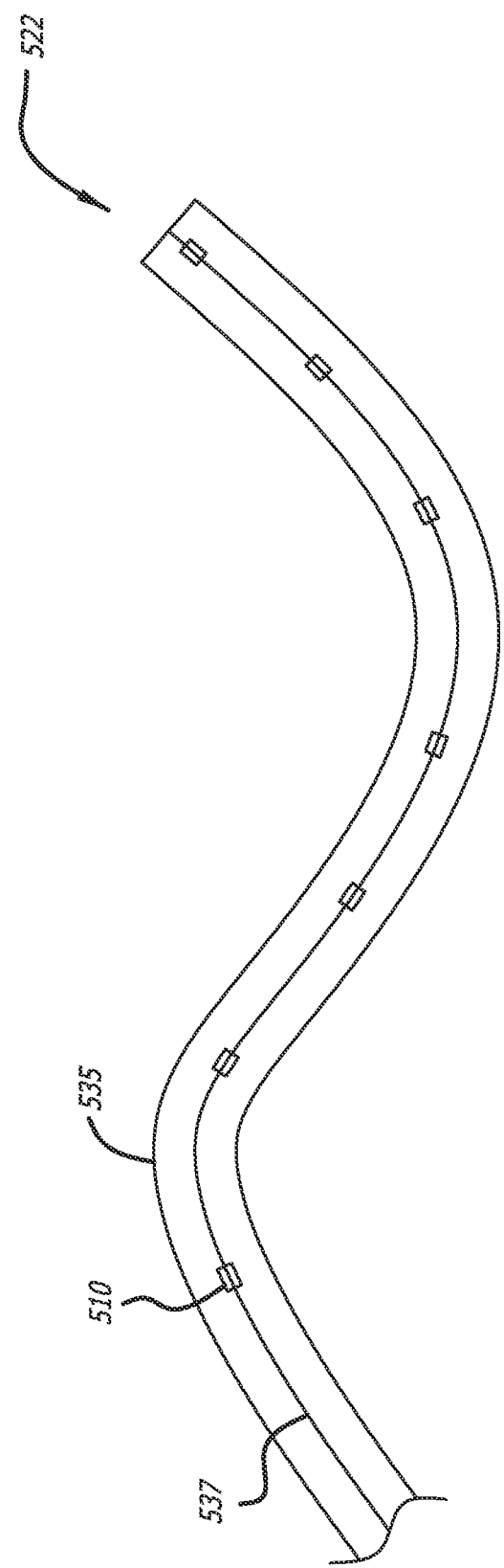
FIG. 5 is an illustration of another embodiment of an optical fiber configured for identifying a blood vessel, in accordance with some embodiments.

Referring to FIG. 5, illustrates a second exemplary embodiment of an optical fiber 535 that can, in certain respects, resemble components of the optical fiber 135 described in connection with FIGS. 1-3B. It will be appreciated that all the illustrated embodiments may have analogous features. Accordingly, like features are designated with like reference numerals, with the leading digits of "5." For instance, the core fibers are designated as "137" in FIGS. 1-3B, and analogous core fibers are designated as "537" in FIG. 5. Relevant disclosure set forth above regarding similarly identified features thus may not be repeated hereafter. Moreover, specific features of the optical fiber 135 and related components shown in FIGS. 1-3B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the optical fiber 535 of FIG. 5. Any suitable combination of the features, and variations of the same, described with respect to the optical fiber 135 and components illustrated in FIGS. 1-3B can be employed with the optical fiber and components of FIG. 5, and vice versa.

The optical fiber 535 includes a number (e.g., 1, 2, 3, or more) of core fibers 537 illustrated as a single core fiber 537 in of FIG. 5. The core fiber 537 includes a number (e.g., 1, 2, 3, or more) of sensors (e.g., reflective gratings) 510 disposed along a length of the optical fiber 535. At least a subset of the core fibers 537 are configured to (i) project light distally away from the distal end 522 of the optical fiber 535 and (ii) receive reflected via the distal end 522. The optical fiber 535 is configured for employment with the probe 120 and the optical fiber 535 is coupled with the console 110 of FIG. 1.

The optical fiber 535 is configured for insertion within the vasculature of the patient and the optical fiber 535 is generally configured to facilitate determination by the state sensing logic 194 that the blood vessel, within which the optical fiber 535 inserted is a vein versus an artery. As such, various subsets of the sensors may be configured to detect/determine different states of the optical fiber 535. One subset of the sensors 510 may be configured to detect/determine a pressure exerted onto the optical fiber 535 adjacent the respective sensors, such as a blood pressure including a pressure pulse, for example. Another subset of the sensors 510 may be configured to detect/determine a temperature of a substance in contact with the optical fiber 535 adjacent the respective sensors, such as a blood or infusate temperature, for example. Another subset of the sensors 510 may be configured to detect/determine a movement (i.e., a change in shape) of the optical fiber 535 or portion thereof. Another subset of the sensors 510 may be configured to detect/determine a longitudinally compressive or tensile strain of the optical fiber 535 or portion thereof.

Figure 6A:
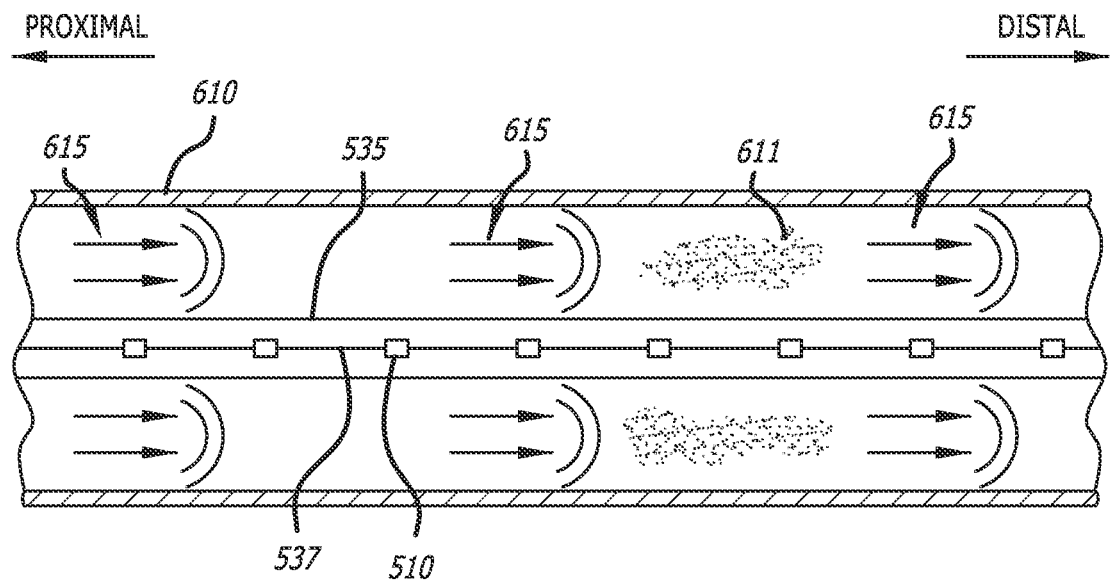
FIG. 6A illustrates an implementation of the optical fiber of FIG. 5 identifying a blood vessel based on pressure pulses, in accordance with some embodiments.

FIG. 6A illustrates a first implementation of the optical fiber 535 in combination with the state sensing logic 194 determining that the blood vessel is a vein or is an artery based on a fluctuating movement of the optical fiber 535 or a portion thereof. FIG. 6A shows the optical fiber 535 disposed within an artery 610. Generally, the flow of arterial blood 611 within the artery 610 includes pressure/flow pulses 615 in accordance with a heartbeat. The pressure/flow pulses 615 define a fluctuating pressure of the arterial blood 611 within the artery in combination with a fluctuating flow rate of the arterial blood 611 along the artery 610. A vein, on the other hand, may include pressure/flow pulses that are significantly decreased with respect to the pressure/flow pulses 615 within the artery 610.

The optical fiber 535 is generally configured to detect the pressure/flow pulses 615 or otherwise determine that the pressure/flow pulses 615 are different than (e.g., greater than) the significantly lower (i.e., having a lower magnitude) pressure/flow pulses of the vein. More specifically, the sensors 510 may define reflected light signals that vary based on a presence versus an absence of pressure/flow pulses 615 along the optical fiber 535. The sensors 510 may define the varying reflected light signals when the blood flows in distal direction with respect to the optical fiber 535 as illustrated. The sensors 510 may also define the varying reflected light signals when the blood flows in an opposite proximal direction with respect to the optical fiber 535.

In some embodiments, the sensors 510 may define the varying reflected light signals based on a strain of the optical fiber 535 induced by the pressure/flow pulses 615. In some embodiments, the strain may be based on a pressure component of the pressure/flow pulse 615 acting on the optical fiber 535 in lateral direction with respect to the optical fiber 535. In other embodiments, the strain may be based on a drag force acting on the optical fiber 535 in a longitudinal direction with optical fiber 535, where the drag force is caused by the flow component of the pressure/flow pulse 615. In still other embodiments, the strain may be based on a combination of the pressure component and the flow component.

The state sensing logic 194 may receive electrical signals related the reflected light signals based on the pressure/flow pulse 615 and define present pulse data therefrom. In some embodiments, the state sensing logic 194 may then compare the present pulse data with one or more limits stored in memory, such as a high limit for vein pulse data or a low limit for arterial pulse data. As a result of the comparison, the state sensing logic 194 may determine that the optical fiber 535 is inserted within the artery 610.

Figure 6B:
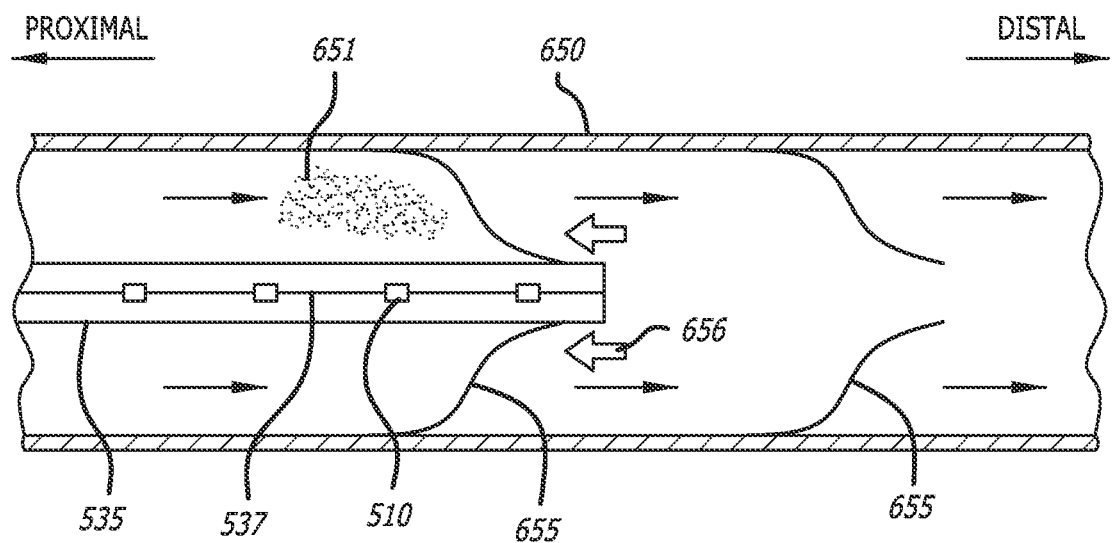
FIG. 6B illustrates an implementation of the optical fiber of FIG. 5 identifying a blood vessel based on engagement of the optical fiber with the check valves of a vein, in accordance with some embodiments.

FIG. 6B illustrates a second implementation of the optical fiber 535 in combination with the state sensing logic 194 determining that the blood vessel is a vein or is an artery based on engagement of the optical fiber 535 with check valves of the vein. Unlike arteries, veins have check valves (i.e., one way valves) that prevent flow of venous blood away from the heart. FIG. 6B shows a vein 650 having venous blood 651 flowing through check valves 655. The optical fiber 535 is shown inserted into the vein 650 in the direction of flow of the venous blood 651. The optical fiber 535 is further shown inserted through one of the check valves 655.

During advancement of the optical fiber 535 along the vein 650, the optical fiber 535 may engage/contact the check valve 655 such that the check valve 655 exerts a force 656 onto the optical fiber 535. The optical fiber 535 experiences a longitudinally directed compressive strain as a result of the exerted force 656. The sensors 510, in turn, may define the varying reflected light signals based on the compressive strain of the optical fiber 535 induced by the exerted force 656.

The state sensing logic 194 may receive electrical signals related the reflected light signals during the insertion process of the optical fiber 535. As the optical fiber 535 engages the check valve 655 during insertion, the electrical signals may indicate a change in the reflected light signals based on the compressive strain resulting from engagement of the optical fiber 535 with the check valve 655 and define present engagement data therefrom. For example, during insertion the state sensing logic 194 may determine a first level of compressive strain as the optical fiber is advanced between adjacent check valves 655 and then determine an increased second level (e.g., a spike) of compressive strain as the optical fiber 535 engages/contacts each check valve 655. In some embodiments, the state sensing logic 194 compare a present difference in magnitude between the second level of compressive strain and the first level of compressive strain with a difference in magnitude stored in memory. As a result of the comparison, the state sensing logic 194 may determine that the optical fiber 535 is inserted within or advanced along the vein 650 versus an artery.

Figure 6C:
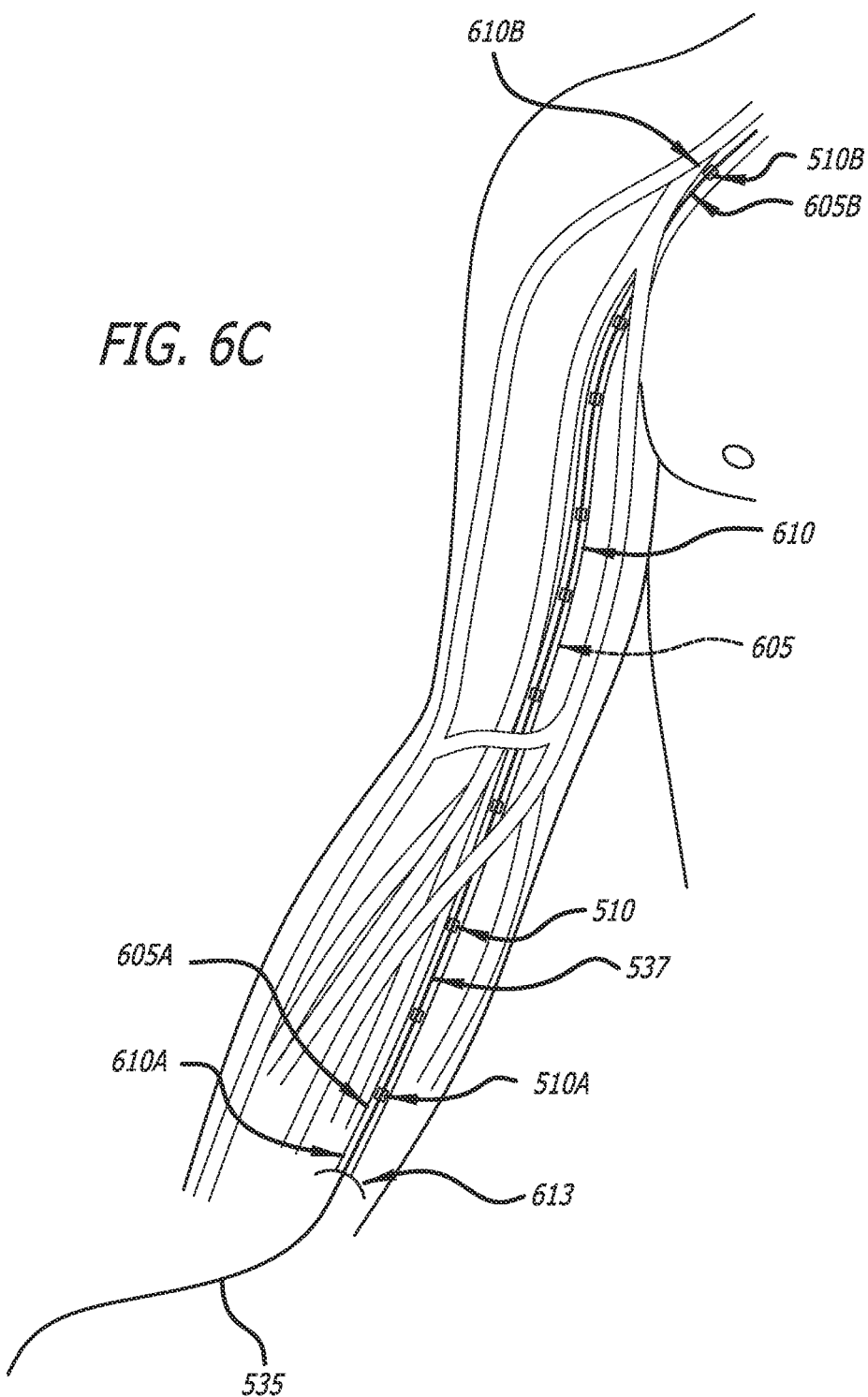
FIG. 6C illustrates an implementation of the optical fiber of FIG. 5 identifying a blood vessel based on a pressure gradient along a length of the optical fiber, in accordance with some embodiments.

FIG. 6C illustrates a third implementation of the optical fiber 535 in combination with the state sensing logic 194 determining that the blood vessel is a vein or is an artery based on a pressure gradient along the optical fiber 535. An arterial blood pressure, i.e., a systolic blood pressure, a diastolic blood pressure, a mean arterial blood pressure or a combination thereof, may generally a decrease along the artery in the direction of arterial blood flow. Conversely, the arterial blood pressure may increase along the artery in the opposite direction of the arterial blood flow. A similar decrease/increase in venous blood pressure along the vein may be significantly less than the decrease/increase of the arterial blood pressure. The difference in the change of blood pressure along an artery versus a vein may be used to differentiate an artery from a vein.

FIG. 6C shows an arm of a patient having an artery 610 extending along the arm. The optical fiber 535 is inserted into the artery 610 at an insertion site 613. The optical fiber 535 is advanced along the artery 610 so as to extend away from the insertion site 513 in a direction opposite to the opposite the flow direction of arterial blood 605, i.e., toward the heart. The optical fiber 535 includes the fiber core 537 having a plurality of sensors 510 distributed therealong, where each sensor 510 is configured to obtain a pressure measurement of the arterial blood 605 at the location adjacent the respective sensor 510. The plurality of sensors 510 includes a first sensor 510A positioned at a first location 610A along the artery 610 and second sensor 510B positioned at a second location 610B, where the first location 610A is downstream of the second location 610B. As the first location 610A is downstream of the second location 610B, a first arterial blood pressure 605A at the location 610A is less than a second arterial blood pressure 605B at the location 610B. Therefore, the second sensor 510B detects the second arterial blood pressure 605B and the first sensor 510A detects the first arterial blood pressure 605A. In a similar fashion, each of the sensors 510 disposed between the second sensor 510B and first sensor 510A detected arterial blood pressures that decreases as the sensors 510 are disposed further from the second sensor 510B toward the first sensor 510A so as to determine a decreasing arterial blood pressure gradient.

The state sensing logic 194 may receive electrical signals related to the reflected light signals from any number of sensors 510 disposed along the optical fiber 535, where the electrical signals indicate a pressure, and as such, may determine a present pressure gradient along an inserted portion of the optical fiber 535. In some embodiments, the state sensing logic 194 may compare the present gradient with a gradient limit stored in memory, and as a result of the comparison, the state sensing logic 194 may determine that the optical fiber 535 is inserted within an artery or is inserted within a vein. For example, if the present gradient exceeds (i.e., has a greater magnitude of slope, either positive or negative) the state sensing logic 194 may determine that the optical fiber 535 is inserted within the artery 610.

Figure 6D:
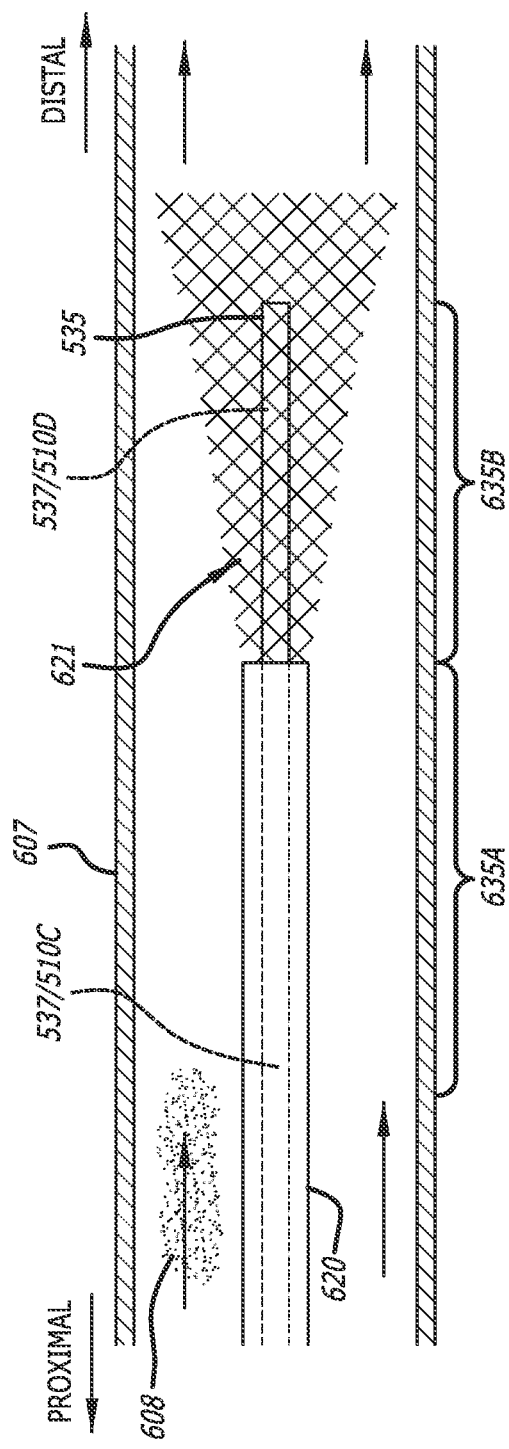
FIGS. 6D-6E illustrate an implementation of the optical fiber of FIG. 5 disposed within a catheter identifying a blood vessel based on a temperature of an infusate delivered via the catheter, in accordance with some embodiments.
Figure 6E:
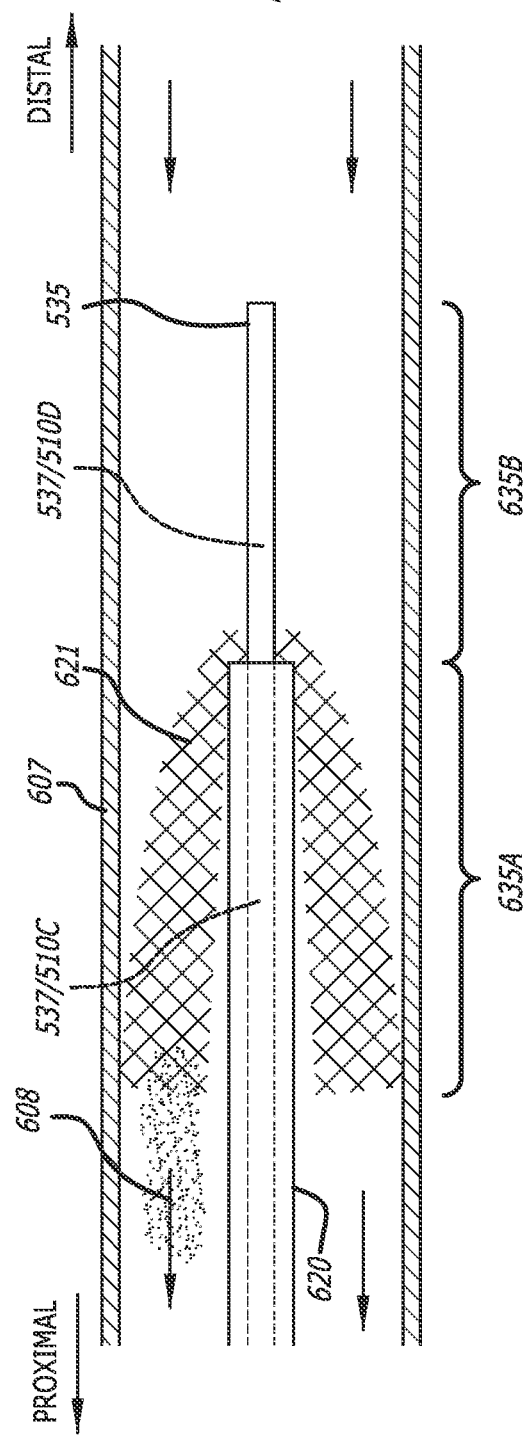

FIGS. 6D-6E illustrate a fourth implementation of the optical fiber 535 in combination with the state sensing logic 194 determining that the blood vessel is a vein or is an artery based on a temperature along the optical fiber 535. As an infusate is delivered to a blood vessel via a catheter, the infusate is generally mixed with the blood downstream of the point of infusion (e.g., the distal end of the catheter). As the infusate may have a temperature different that the blood, the temperature of the blood portion having infusate mixed therewith (i.e., the blood portion downstream of the infusion point) may be measurably different than the temperature of the blood portion having no infusate mixed therewith (i.e., the blood portion upstream of the infusion point). As such, the direction of blood flow within a blood vessel may be determined via temperature measurements of the blood adjacent the distal end of a catheter during infusate delivery.

In the illustrated embodiment, at least a subset of the sensors 510 of the optical fiber 535 are configured to detect temperature, e.g., determine a temperature of a substance, such as blood, for example, adjacent the optical fiber 535 at the locations of the respective sensors 510. In some embodiments, determining a temperature may include the sensors 510 detecting a temperature induced strain of the optical fiber 535 due to thermal expansion/contraction.

Each of the FIGS. 6D and 6E illustrate a catheter 620 delivering an infusate 621 to a blood vessel 607. The optical fiber 535 is inserted within a lumen of the catheter 607 such that a first section 635A of the optical fiber 535 along with a first subset 510C of sensors 510 are disposed within the lumen of the catheter 620. The optical fiber 535 extends beyond a distal end of the catheter 607 such that a second section 635B of the optical fiber 535 along with a second subset 510D of sensors 510 are disposed outside of the lumen of the catheter 620. Each of the first and second subsets 510C, 510D of the sensors 510 are configured to determine temperature. As the first section 635A is disposed within the lumen of the catheter 620, the first subset 510C of sensors 510 determining temperatures consistent with a temperature of the infusate 621.

FIG. 6D illustrates a first instance, where the blood 608 is flowing in a distal direction with respect to the optical fiber 535. As such, the infusate 621 flows distally away from the distal end of the catheter 620 mixing with the blood 621 along the second section 635B of the optical fiber 535. As such, the second subset 510D of sensors 510 determine temperatures of a mixture of the blood 608 and the infusate 621.

FIG. 6E illustrates a second instance, where the blood 608 is flowing in a proximal direction with respect to the optical fiber 535. As such, the infusate 621 flows proximally away from the distal end of the catheter 620 mixing with the blood 621 along on outside surface of the catheter 620. As such, the second subset 510D of sensors 510 determine temperatures of the blood 608 prior to mixing with the infusate 621.

By way of summary, in the instance of FIG. 6D the first subset 510C of sensors 510 determine a temperature of infusate 621 and the second subset 510C of sensors 510 determine a temperature of infusate 621 mixed with the blood 608, while in the instance of FIG. 6E the first subset 510C of sensors 510 determine a temperature of infusate 621 and the second subset 510C of sensors 510 determine a temperature of the blood 608 alone. As such, a first determined temperature difference between the first and second subsets 510C, 510D in the first instance may be different than a second determined temperature difference between the first and second subsets 510C, 510D in the second instance.

The state sensing logic 194 may receive electrical signals related to the reflected light signals from any number of sensors 510 disposed along the optical fiber 535, where the electrical signals indicate a temperature and as such, may determine present temperatures along the first and second sections the optical fiber 535 during delivery of the infusate 621. The state sensing logic 194 may then determine present temperature difference between temperatures along the first and second sections the optical fiber 535. In some embodiments, the state sensing logic 194 may compare the present temperature with a temperature difference stored in memory, and as a result of the comparison, the state sensing logic 194 may determine that (i) the optical fiber 535 is inserted within the blood vessel 607 in the same direction as the flow of the blood 608 or (ii) the optical fiber 535 is inserted within the blood vessel 607 in the opposite direction to the flow of the blood 608. As the direction of the optical fiber 535 with respect to the body (e.g., toward or away from the heart) may be known, the state sensing logic 194 may determine that the optical fiber 535 is inserted within an artery or is inserted within a vein.

By way of a similar implementation, the state sensing logic may analyze temperature differences during delivery and non-delivery of the infusate 621. The state sensing logic 194 may receive electrical signals related to the reflected light signals from any number of sensors 510 disposed along the optical fiber 535, where the electrical signals indicate a temperature and as such, may determine a first present temperature along the second section 635B of the optical fiber 535 during delivery of the infusate 621. The state sensing logic 195 may also determine a second present temperature along the second section 635B of the optical fiber 535 during non-delivery of the infusate 621. The state sensing logic 194 may then determine a present temperature difference between first and second present temperatures. In some embodiments, the state sensing logic 194 may compare the present difference with a temperature difference stored in memory, and as a result of the comparison, the state sensing logic 194 may determine that (i) the optical fiber 535 is inserted within the blood vessel 607 in the same direction as the flow of the blood 608 or the optical fiber 535 is inserted within the blood vessel 607 in the opposite direction to the flow of the blood 608. As the direction of the optical fiber 535 with respect to the body (e.g., toward or away from the heart) may be known, the state sensing logic 194 may determine that the optical fiber 535 is inserted within an artery or is inserted within a vein.

FIGS. 6F-6G illustrate a fifth implementation of the optical fiber 535 in combination with the state sensing logic 194 determining that the blood vessel is a vein or is an artery based on reflections of incident light that are shifted toward the red or blue spectrum. The optical fiber 535 may be advanced along a blood vessel in the same direction as the blood flow or in the opposite direction to the blood flow. In accordance with the doppler effect, reflections of incident light projected onto particles within the blood may shift toward the red spectrum (i.e., longer wavelengths) when the blood is flowing away from the light source. Conversely, reflections of incident light projected onto particles within the blood may shift toward the blue spectrum (i.e., shorter wavelengths) when the blood is flowing toward from the light source. As such, an analysis of the reflected light may indicate a direction of blood flow.

Each of the FIGS. 6F and 6G illustrate the optical fiber 535 inserted within the blood vessel 607. The optical fiber 535 such that a distal end 638 of the optical fiber 535 is disposed within the blood 608 flowing within the blood vessel 607. Incident light 641 is propagated distally along the optical fiber 535 and projected distally away from the distal end 638 into the blood 608, i.e., onto particles within the blood 608. The incident light 641 reflects off of the particles within the blood 608 to generate reflected light that is received by the optical fiber 535 and propagated proximally back along the optical fiber 535.

FIG. 6F illustrates a first instance, where the blood 608 is flowing in a distal direction with respect to the optical fiber 535. As such, the incident light 641 is projected onto blood particles that are moving away from the distal end 638 generating reflected light 642 that has shifted toward the red spectrum with respect to the incident light 641.

FIG. 6G illustrates a second instance, where the blood 608 is flowing in a proximal direction with respect to the optical fiber 535. As such, the incident light 641 is projected onto blood particles that are moving toward the distal end 638 generating reflected light 643 that has shifted toward the blue spectrum with respect to the incident light 641.

The state sensing logic 194 may receive electrical signals related to the reflected light propagated proximally along the optical fiber 535, where the electrical signals indicate a wavelength of the reflected light. In some embodiments, the state sensing logic 194 may compare the present wavelength of the reflected light with a wavelength of the incident light. As a result of the comparison, the state sensing logic 194 may determine that (i) the optical fiber 535 is inserted within the blood vessel 607 in the same direction as the flow of the blood 608 or (ii) the optical fiber 535 is inserted within the blood vessel 607 in the opposite direction to the flow of the blood 608. As the direction of the optical fiber 535 with respect to the body (e.g., toward or away from the heart) may be known, the state sensing logic 194 may determine that the optical fiber 535 is inserted within an artery or is inserted within a vein.

Figure 7:
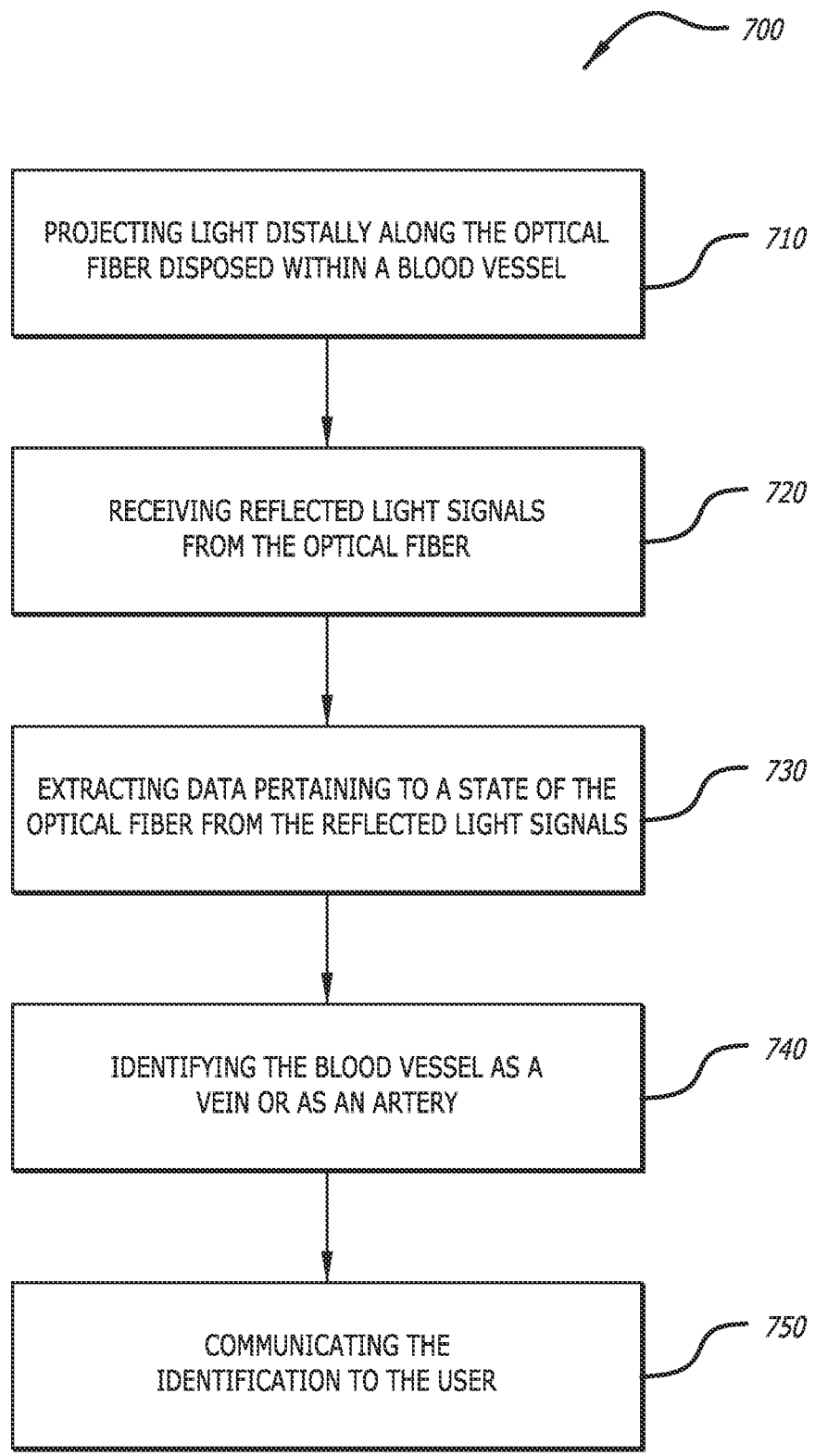
FIG. 7 illustrates a flow chart of a method of the system for identifying a blood vessel, in accordance with some embodiments.

FIG. 7 illustrates a block diagram of a method 700 of identifying a blood vessel as a vein or an artery. The method 700 may, according to some embodiments, include all or a subset of the following steps or processes performed by the system 100 as described below. Having the optical fiber disposed within a blood vessel, the system 100 may project a light distally along the optical fiber (block 710). Projecting the light may include propagating the light along one or more fiber cores to any or all sensors disposed along the fiber cores and/or to the distal end of the optical fiber. Projecting the light may include may further include projecting the light distally away from the distal end of the optical fiber so as to impinge on substances or objects, such as blood, or particles within the blood while the blood is flowing toward or away from the distal end.

The system receives reflected light signals from the optical fiber (block 720). In other words, the projected light may reflect off a number of sensors or other objects and propagate proximally along the optical fiber to the optical receiver. The reflected light signals may include spectral portions of a broad band projected light or shifts in wavelength of the projected light. The reflected light signals are based on a state of or a condition experienced by the optical fiber.

The logic of the system 100 extracts present data from the reflected light signals (block 730). The logic analyzes the present data as it pertains the state of the optical fiber. Analyzing the data may include comparing the present data with other data or limits stored in the memory. As a result of the comparison or the analysis generally, the logic makes determinations/conclusions regarding the state of the optical fiber in conjunction with physiological conditions of the patient or more specifically the blood vessel.

The logic my identify the blood vessel as a vein or as an artery based on the analysis of the data (block 740). Generally speaking, the logic may analyze the data to determine if the state of the optical fiber is consistent with placement of the optical fiber within a vein or within an artery.

The analysis may include any one or a combination of the subprocesses described below to identify the blood vessel. A subprocess may include projecting the incident light distally away from the distal end of the optical fiber into the blood and receiving a reflected light signal emanating from particles within the blood via the optical fiber. The incident light has a defined wavelength. The reflect light signal may contain light at a shifted wavelength consistent with movement of the particles within the blood moving either toward or away from the distal end of the optical fiber. The analysis may then determine that blood is flowing in the distal direction or alternatively in the proximal direction with respect to the optical fiber consistent with the shift in wavelength. As the direction of the optical fiber with respect to the heart may be known, the analysis may include identifying the blood vessel as a vein or as an artery based on the wavelength shift.

In accordance with further subprocesses described below, the optical fiber may include a number of core fibers, where at least one of the fiber cores includes a plurality of sensors distributed along a longitudinal length of the optical fiber, and where each sensor of the plurality of sensors is configured to (i) reflect a light signal of a different spectral width based on received incident light, and (ii) change a characteristic of the reflected light signal based on a state of the optical fiber. As such, the reflected light signal(s) is generated by a sensor of the optical fiber.

In some instances, pressure pulses within an artery may cause fluctuating movement of at least a portion of the optical fiber. As such, another subprocess may include extracting data from the at least one reflected light signal, where the data is consistent with fluctuating movement of the optical fiber. The subprocess may further include identifying the blood vessel as a vein if the present fluctuating movement data is consistent with a vein or as an artery if the present fluctuating movement data is consistent with an artery.

According to another subprocess, the state of the optical fiber includes a compressive strain of the optical fiber, and the subprocess includes extracting compressive strain data from at least one reflected light signal, and identifying the blood vessel as a vein if the compressive strain data is consistent with engagement of the distal end of the optical fiber with the check valves of a vein during advancement of the optical fiber or as an artery if the compressive strain data is inconsistent with engagement of the distal end of the optical fiber with the check valves of a vein during advancement of the optical fiber.

According to another subprocess, the state of the optical fiber includes pressure fluctuations exerted on the optical fiber and the subprocess includes extracting pressure fluctuation data from at least one reflected light signal, and identifying the blood vessel as a vein if the pressure fluctuation data is consistent with the pressure fluctuations of a vein or as an artery if the pressure fluctuation data is inconsistent with pressure fluctuations of an artery.

According to another subprocess, the state of the optical fiber includes pressure fluctuations exerted on the optical fiber along a length of the optical fiber disposed within the blood vessel, and the subprocess further includes receiving a plurality of reflected light signals generated from a plurality of sensors disposed along the length of the optical fiber disposed within the blood vessel, where each reflected light signal is based on a pressure exerted on the optical fiber adjacent the respective sensor. The subprocess further includes identifying the blood vessel as an artery if the pressure wave data is consistent with placement of the optical fiber within an artery or as a vein if the pressure wave data is inconsistent with placement of the optical fiber within an artery.

According to another subprocess, the state of the optical fiber includes a pressure gradient exerted on the optical fiber along a length of the optical fiber disposed within the blood vessel, and reflected light signals generated from a plurality of sensors disposed along the length of the optical fiber disposed within the blood vessel are based on a pressures exerted on the optical fiber adjacent the respective sensors, where the extracted data represents the pressure gradient. The subprocess further includes identifying the blood vessel as an artery if the pressure gradient is consistent with an artery or as a vein if the pressure gradient is inconsistent with an artery.

According to another subprocess, the optical fiber is inserted within the blood vessel in a direction toward a heart of a patient, the optical fiber is inserted within a lumen of a catheter, and the catheter is delivering an infusate to the blood vessel. The state of the optical fiber includes a first temperature experienced by a first section of the optical fiber disposed within the catheter and a second temperature experienced by a second section of the optical fiber extending distally beyond a distal end of the catheter. Extracted temperature difference data represents a difference between the first and second temperatures. The subprocess further includes identifying the blood vessel as a vein if the temperature difference data is consistent venous flow toward the heart or as an artery if the temperature difference data is consistent arterial flow away the heart.

According to another subprocess, the optical fiber is inserted within the blood vessel in a direction toward a heart of a patient, the optical fiber extends along a catheter, where the catheter is configured to deliver an infusate to the blood vessel. The state of the optical fiber includes a first temperature experienced by a section of the optical fiber extending beyond a distal end of the catheter during non-delivery of the infusate and a second temperature experienced by the section during delivery of the infusate. Extracted temperature difference data represents the temperature difference between first and second temperatures and the subprocess further includes identifying the blood vessel as a vein if the temperature difference data is consistent venous flow toward the heart or as an artery if the temperature difference data is consistent arterial flow away the heart.

After identifying the blood vessel, the logic may communicate the result, i.e., the identification of the blood vessel to the user (block 750), such as providing visual notification via the display, for example.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A medical system, comprising:
    an optical fiber configured for insertion within a blood vessel, the optical fiber having one or more core fibers extending along a longitudinal length of the optical fiber, each of the one or more core fibers including a plurality of sensors distributed along the longitudinal length and each sensor of the plurality of sensors configured to (i) reflect a light signal of a different spectral width based on received incident light, and (ii) change a characteristic of the reflected light signal based on a state of the optical fiber; and
    a console operatively coupled with the optical fiber, the console including a light source, an optical receiver, one or more processors, and a non-transitory computer-readable medium having stored thereon logic that, when executed by the one or more processors, causes operations including:
        projecting a light distally along the optical fiber;
        receiving at least one reflected light signal from the optical fiber, wherein the at least one reflected light signal is generated by a sensor of the optical fiber;
        determining, based on the at least one reflected light signal, that the blood vessel is a vein or is an artery; and
        communicating a result of the determining to a user.

2. The system of claim 1, wherein:
    the optical fiber is inserted within the blood vessel in a direction toward a heart of a patient, and
    the operations further include:
        projecting a light defining a first wavelength distally away from a distal end of the optical fiber into blood of the blood vessel;
        receiving a reflected light signal having a second wavelength via the distal end;
        extracting from the reflected light signal a present wavelength shift between the first wavelength and the second wavelength;
        comparing the present wavelength shift with one or more wavelength shift limits stored in the non-transitory computer-readable medium; and
        determining, as a result of the comparing, that the blood vessel is a vein or is an artery.

3. The system of claim 1, wherein:
    the state of the optical fiber includes a fluctuating movement of at least a portion of the optical fiber, and
    the operations further include:
        extracting from the at least one reflected light signal present fluctuating movement data;
        comparing the present fluctuating movement data with a fluctuating movement limit stored in the non-transitory computer-readable medium; and
        determining, as a result of the comparing, that the blood vessel is a vein or is an artery.

4. The system of claim 1, wherein:
    the state of the optical fiber includes a compressive strain of the optical fiber caused by engagement of the optical fiber with one or more check valves of the blood vessel during advancement of the optical fiber along the blood vessel, and
    the operations further include:
        extracting from the at least one reflected light signal present compressive strain data;
        comparing the present compressive strain data with a compressive strain limit stored in the non-transitory computer-readable medium; and
        determining, as a result of the comparing, that the blood vessel is a vein or is an artery.

5. The system of claim 1, wherein:
    the state of the optical fiber includes pressure fluctuations exerted on the optical fiber, and
    the operations further include:
        extracting from the at least one reflected light signal present pressure fluctuation data;
        comparing the present pressure fluctuation data with a pressure fluctuation limit stored in the non-transitory computer-readable medium; and
        determining, as a result of the comparing, that the blood vessel is a vein or is an artery.

6. The system of claim 1, wherein:
    the state of the optical fiber includes pressure fluctuations exerted on the optical fiber along a length of the optical fiber disposed within the blood vessel, the pressure fluctuations caused by a pressure wave traveling longitudinally along the optical fiber, and
    the operations further include:
        receiving a plurality of reflected light signals generated from the plurality of sensors disposed along the length of the optical fiber disposed within the blood vessel, each reflected light signal based on a pressure exerted on the optical fiber adjacent each respective sensor;
        extracting from the plurality of reflected light signals present pressure wave data;
        comparing the present pressure wave data with one or more pressure wave limits stored in the non-transitory computer-readable medium; and
        determining, as result of the comparing, that the blood vessel is a vein or is an artery.

7. The system of claim 1, wherein:
    the state of the optical fiber includes a pressure gradient exerted on the optical fiber along a length of the optical fiber disposed within the blood vessel, and
    the operations further include:

receiving a plurality of reflected light signals generated from the plurality of sensors disposed along the length of the optical fiber disposed within the blood vessel, each reflected light signal based on a pressure exerted on the optical fiber adjacent the respective sensor;

extracting from the plurality of reflected light signals a present pressure gradient data;

comparing the pressure gradient data with a pressure gradient limit stored in the non-transitory computer-readable medium; and determining, as a result of the comparing, that the blood vessel is a vein or is an artery.

8. The system of claim 1, wherein:

the optical fiber is inserted within the blood vessel in a direction toward a heart of a patient, the optical fiber is inserted within a lumen of a catheter, the catheter delivering an infusate to the blood vessel, the state of the optical fiber includes:
 a first temperature experienced by a first section of the optical fiber disposed within the catheter; and
 a second temperature experienced by a second section of the optical fiber extending distally beyond a distal end of the catheter, and the operations further include:
 receiving a first reflected light signal from a first sensor disposed along the first section, the first reflected light signal based on the first temperature;
 receiving a second reflected light signal from a second sensor disposed along the second section, the second reflected light signal based on the second temperature;
 extracting from the first reflected light signal and the second reflected light signal a present temperature difference data between the first temperature and the second temperature;
 comparing the present temperature difference data with a temperature difference limit stored in the non-transitory computer-readable medium; and
 determining, as a result of the comparing, that the blood vessel is a vein or is an artery.

9. The system of claim 1, wherein:

the optical fiber is inserted within the blood vessel in a direction toward a heart of a patient, the optical fiber extends along a catheter, the catheter configured to deliver an infusate to the blood vessel, the state of the optical fiber includes:
 a first temperature experienced by a section of the optical fiber extending beyond a distal end of the catheter during non-delivery of the infusate; and
 a second temperature experienced by the section of the optical fiber during delivery of the infusate; and the operations further include:
 receiving a first reflected light signal from a sensor disposed along the section during non-delivery of the infusate, the first reflected light signal based on the first temperature;
 receiving a second reflected light signal from the sensor, the second reflected light signal based on the second temperature;
 extracting from the first reflected light signal and the second reflected light signal present temperature difference data between the first temperature and the second temperature;
 comparing the present temperature difference data with a temperature difference limit stored in the non-transitory computer-readable medium; and
 determining, as a result of the comparing, that the blood vessel is a vein or is an artery.

10. The system of claim 1, wherein the optical fiber is coupled with an elongate medical device, the elongate medical device including a catheter, a stylet, a probe, or a guidewire.

11. A method performed by a medical system of identifying a blood vessel, comprising:

projecting incident light distally along an optical fiber of the medical system, the optical fiber disposed within the blood vessel, the optical fiber including a number of core fibers, at least one of the number of core fibers including a plurality of sensors distributed along a longitudinal length of the optical fiber, wherein each sensor of the plurality of sensors is configured to (i) reflect a light signal of a different spectral width based on received incident light, and (ii) change a characteristic of the reflected light signal based on a state of the optical fiber;

receiving at least one reflected light signal from the optical fiber, wherein the at least one reflected light signal is generated by a sensor of the optical fiber;

identifying the blood vessel as a vein or as an artery based on the at least one reflected light signal; and communicating an identification of the blood vessel to a user.

12. The method of claim 11, comprising:

projecting the incident light distally away from a distal end of the optical fiber, the incident light having a defined wavelength;

receiving a reflected light signal emanating from particles within the blood vessel via the optical fiber;

determining a wavelength shift between the incident light and the reflected light signal; and identifying the blood vessel as a vein or as an artery based on the wavelength shift.

13. The method of claim 11, wherein the state of the optical fiber includes a fluctuating movement of at least a portion of the optical fiber, the method further comprising:

extracting from the at least one reflected light signal present fluctuating movement data; and identifying the blood vessel as a vein or as an artery based on the present fluctuating movement data.

14. The method of claim 11, wherein the state of the optical fiber includes a compressive strain of the optical fiber caused by engagement of the optical fiber with one or more check valves along the blood vessel during advancement of the optical fiber along the blood vessel, the method further comprising:

extracting from the at least one reflected light signal present compressive strain data; and identifying the blood vessel as a vein or as an artery based on the present compressive strain data.

15. The method of claim 11, wherein the state of the optical fiber includes a pressure fluctuation exerted on the optical fiber, the method further comprising:

extracting from the at least one reflected light signal present pressure fluctuation data; and identifying the blood vessel as a vein or as an artery based on the present pressure fluctuation data.

16. The method of claim 11, wherein the state of the optical fiber includes a pressure fluctuations exerted on the optical fiber along a length of the optical fiber disposed within the blood vessel, the pressure fluctuations caused by a pressure wave traveling longitudinally along the optical fiber, the method further comprising:

receiving a plurality of reflected light signals generated from the plurality of sensors disposed along the length of the optical fiber disposed within the blood vessel, each reflected light signal based on a pressure exerted on the optical fiber adjacent each respective sensor;

extracting from the plurality of reflected light signals present pressure wave data; and identifying the blood vessel as a vein or as an artery based on the present pressure wave data.

17. The method of claim 11, wherein the state of the optical fiber includes a pressure gradient exerted on the optical fiber along a length of the optical fiber disposed within the blood vessel, the method further comprising:

receiving a plurality of reflected light signals generated from the plurality of sensors disposed along the length of the optical fiber disposed within the blood vessel, each reflected light signal based on a pressure exerted on the optical fiber adjacent each respective sensor;

extracting from the plurality of reflected light signals present pressure gradient data; and identifying the blood vessel as a vein or as an artery based on the present pressure gradient data.

18. The method of claim 11, wherein:

the optical fiber is inserted within the blood vessel in a direction toward a heart of a patient, the optical fiber is inserted within a lumen of a catheter, the catheter delivering an infusate to the blood vessel, the state of the optical fiber includes:
  a first temperature experienced by a first section of the optical fiber disposed within the catheter; and
  a second temperature experienced by a second section of the optical fiber extending distally beyond a distal end of the catheter, and the method further includes:
  receiving a first reflected light signal from a first sensor disposed along the first section, the first reflected light signal based on the first temperature;
  receiving a second reflected light signal from a second sensor disposed along the second section, the second reflected light signal based on the second temperature;
  extracting from the first reflected light signal and the second reflected light signal present temperature difference data between the first temperature and the second temperature; and
  identifying the blood vessel as a vein or as an artery based on the present temperature difference data.

19. The method of claim 11, wherein:

the optical fiber is inserted within the blood vessel in a direction toward a heart of a patient, the optical fiber extending along a catheter, the catheter configured to deliver an infusate to the blood vessel, the state of the optical fiber includes:
  a first temperature experienced by a section of the optical fiber extending beyond a distal end of the catheter during non-delivery of the infusate; and
  a second temperature experienced by the section during delivery of the infusate; and the method further includes:
  receiving a first reflected light signal from a sensor disposed along the section during non-delivery of the infusate, the first reflected light signal in based on the first temperature;
  receiving a second reflected light signal from the sensor, the second reflected light signal based on the second temperature during delivery of the infusate;
  extracting from the first reflected light signal and the second reflected light signal present temperature difference data between the first temperature and the second temperature; and
  identifying the blood vessel as a vein or as an artery based on the present temperature difference data.

20. The method of claim 11, wherein the optical fiber is coupled with an elongate medical device, the elongate medical device including a catheter, a stylet, a probe, or a guidewire.

* * * * *